United States Patent [19]

Aldous et al.

[11] Patent Number: 5,618,821
[45] Date of Patent: Apr. 8, 1997

[54] THERAPEUTIC PHENOXYALKYLHETEROCYCLES

[75] Inventors: David J. Aldous, Glenmore; Thomas R. Bailey, Phoenixville; Guy D. Diana, Pottstown; Gee-Hong Kuo, Blue Bell; Theodore J. Nitz, Pottstown, all of Pa.

[73] Assignee: Sanofi, S.A., Paris Cedex, France

[21] Appl. No.: 451,692

[22] Filed: May 26, 1995

Related U.S. Application Data

[63] Continuation of Ser. No. 242,508, May 13, 1994, abandoned.

[51] Int. Cl.⁶ .................. A61K 31/44; A61K 31/505; C07D 213/16; C07D 239/26
[52] U.S. Cl. ............ 514/277; 546/277.4; 546/266; 546/271.4; 546/272.1; 546/272.4; 546/272.7; 546/275.4; 546/113; 546/280.4; 546/152; 546/268.4; 546/271.7; 546/267.7; 546/268.7; 546/269.1; 546/270.1; 546/314; 546/281.4; 546/339; 546/269.7; 546/271.1; 546/283.4; 514/256; 514/269; 514/300; 514/311; 514/314; 514/338; 514/340; 514/354; 514/406; 514/415; 544/242; 544/333; 544/335; 548/373.1; 548/509
[58] Field of Search .................... 514/256, 269, 514/300, 311, 277, 406, 415, 314, 338, 340, 354; 544/298, 332, 315, 242, 333, 335; 546/122, 152, 113, 271, 276, 277, 314, 339; 548/509, 373.1

[56] References Cited

U.S. PATENT DOCUMENTS

| | | | |
|---|---|---|---|
| 4,843,087 | 6/1989 | Diana | 514/374 |
| 4,857,539 | 8/1989 | Diana et al. | 514/378 |
| 4,861,791 | 8/1989 | Diana et al. | 514/374 |
| 4,861,971 | 8/1989 | Chan | 235/384 |
| 4,939,267 | 7/1990 | Diana | 548/237 |
| 4,942,241 | 7/1990 | Diana et al. | 548/131 |
| 4,945,164 | 7/1990 | Diana | 548/247 |
| 5,002,960 | 3/1991 | Diana | 514/378 |
| 5,051,437 | 9/1991 | Diana | 514/365 |
| 5,110,821 | 5/1992 | Diana | 514/364 |
| 5,242,924 | 9/1993 | Diana | 514/252 |

FOREIGN PATENT DOCUMENTS

WO92/05163   4/1992   WIPO.

*Primary Examiner*—Yogendra N. Gupta
*Attorney, Agent, or Firm*—Paul E. Dupont; William J. Davis

[57] ABSTRACT

Compounds of the formula

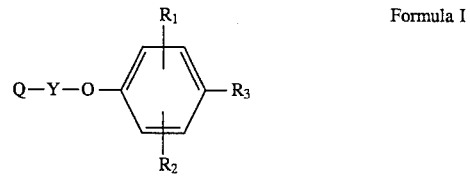

Formula I wherein

Q is chosen from the group consisting of pyridyl, pyrazyl, pyrimidyl, quinolyl, indolyl and 7-azaindolyl or any of these substituted with one or two substituents;

Y is an alkylene bridge of 3–9 carbon atoms;

$R_1$ and $R_2$ are each independently chosen from hydrogen, halo, alkyl, alkenyl, amino, alkylthio, hydroxy, hydroxyalkyl, alkoxyalkyl, alkylthioalkyl, alkylsulfinylalkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkoxycarbonyl, alkyltetrazolyl, substituted or unsubstituted phenyl or heterocyclyl, the N-oxide thereof, or a pharmaceutically acceptable acid addition salt thereof is an effective antipicornaviral agent.

19 Claims, No Drawings

THERAPEUTIC PHENOXYALKYLHETEROCYCLES

This application is a continuation of application Ser. No. 08/242,508, filed May 13, 1994, now abandoned.

BACKGROUND OF THE INVENTION a) Field of the Invention

This invention relates to novel heterocyclic substituted phenoxyalkylpyridines, phenoxyalkylpyridazines and phenoxyalkylpyridimines, to methods of preparation thereof and to methods of use thereof as antipicornaviral agents.

b) Information Disclosure Statement

Published PCT application number WO92/05163 discloses compounds of formula

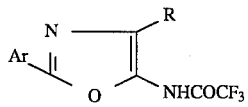

stated to be useful in treating diabetic conditions. Specifically disclosed is N-[2-(4-(2-hydroxy-2-phenyl ethoxy)phenyl)5-oxazolyl]-2,2,2-trifluoro acetamide.

SUMMARY OF THE INVENTION

It has now been found that compounds of Formula I are effective antipicornaviral agents. Accordingly, the present invention relates to a compound of the formula

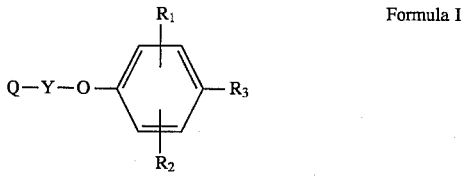

Formula I wherein

Q is chosen from the group consisting of pyridyl, pyrazinyl, pyrimidinyl, quinolyl, indolyl and 7-azaindolyl or any of these substituted with one or two substitutents chosen from hydrogen, alkyl, alkoxy, hydroxy, halo, cyano, nitro, hydroxyalkyl, alkoxyalkyl, alkanoyl, fluoroalkyl or the N-oxide of any of the preceding;

Y is an alkylene bridge of 3–9 carbon atoms;

$R_1$ and $R_2$ are each independently chosen from hydrogen, halo, alkyl, alkenyl, amino, alkylthio, hydroxy, hydroxyalkyl, alkoxyalkyl, alkylthioalkyl, alkylsulfinylalkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkoxycarbonyl, alkyltetrazolyl, phenyl or heterocyclyl chosen from benzoxazolyl, benzathiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, tetrazolyl, thiophenyl, pyridyl, pyrimidinyl, pyrazinyl, pyridazinyl or substituted phenyl or substituted heterocyclyl wherein the substitution is with alkyl, alkoxyalkyl, cycloalkyl, haloalkyl, hydroxyalkyl, alkoxy, hydroxy, furyl, phenyl, thienyl or fluoroalkyl;

or the N-oxide thereof;

or a pharmaceutically acceptable acid addition salt thereof.

The invention also relates to compositions for combating picornaviruses comprising an antipicornavirally effective amount of a compound of Formula I with a suitable carrier or diluent, and to methods of combating picornaviruses therewith, including the systemic treatment of picornaviral infections in a mammalian host.

DETAILED DESCRIPTION OF PREFERRED EMBODIMENTS

Compounds of Formula I are useful as antipicornaviral agents, and are further described hereinbelow.

Alkyl and alkoxy mean aliphatic radicals, including branched radicals, of from one to five carbon atoms. Thus the alkyl moiety of such radicals include, for example methyl, ethyl, propyl, isopropyl, n-butyl, sec-butyl, t-butyl, pentyl and the like.

Cycloalkyl means an alicyclic radical having from three to seven carbon atoms as illustrated by cyclopropyl, cyclobutyl, cyclopentyl, cycloheptyl, and cyclohexyl; and Halo means bromo, chloro, iodo or fluoro.

Heterocyclyl or Het refers to a 5 or 6 membered carbon based heterocycle radical, having from one to about four nitrogen atoms and/or one oxygen or sulfur atom, provided that no two oxygen and/or sulfur atoms are adjacent in the heterocycle. Examples of these include furyl, oxazolyl, isoxazolyl, pyrazyl, imidazolyl, thiazolyl, tetrazolyl, thienyl, pyridyl, oxadiazolyl, thiadiazolyl, triazinyl, pyrimidinyl and the like.

The term heterocyclyl includes all known isomeric radicals of the described heterocycles unless otherwise specified, for example, thiadiazolyl encompasses 1,3,4-thiadiazol-2-yl, 1,2,4-thiadiazol-5-yl, and 1,2,4-thiadiazol-3-yl; thiazolyl encompasses 2-thiazolyl, 4-thiazolylyl and 5-thiazolyl and the other known variations of known heterocyclyl radicals. Thus any isomer of a named heterocycle radical is contemplated. These heterocycle radicals can be attached via any available nitrogen or carbon, for example, tetrazolyl contemplates 5-tetrazolyl or tetrazolyl attached via any available nitrogen of the tetrazolyl ring; furyl encompasses furyl attached via any available carbon, etc. The preparation of such isomers are well known and well within the scope of skilled artisan in medicinal or organic chemistry.

Certain heterocycles can exist as tautomers, and the compounds as described, while not explicity describing each tautomeric form, are meant to embrace each and every tautomer. For example, pyridinones and hydroxy pyridines, are tautomers, thus for convenience in formula I, $R_3$ is referred to as hydroxy, and it is understood thereby that pyridinones (or tautomers of any analogous heterocycle) are specifically intended.

In the use of the terms hydroxyalkyl and alkoxyalkyl, it is understood that the hydroxy and alkoxy groups can occur at any available position of the alkyl. Thus hydroxyalkyl and alkoxyalkyl include, for example, hydroxymethyl, 1-hydroxyethyl, 2-hydroxyethyl, 2-hydroxypropyl, 2-hydroxyisopropyl, 2-, 3-, 4- and 5-hydroxypentyl and the like; alkoxy refers to the corresponding alkyl ethers thereof.

In the use of the term hydroxyalkoxy, it is understood that the hydroxy group can occur at any available position of the alkoxy other than the C-1 (geminal) position. Thus hydroxyalkoxy includes, for example, 2-hydroxyethoxy, 2-hydroxypropoxy, 2-hydroxyisopropoxy, 5-hydroxypentoxy and the like.

Alkylene refers to a linear or branched divalent hydrocarbon radical of from 1 to about 5 carbon atoms such as methylene, 1,2-ethylene, 1,3-propylene, 1,4-butylene, 1,5-pentylene, 1,4-(2-methyl)butylene and the like. It can also contain unsaturation, including alkenyl and alkynyl linkages.

Halogen refers to the common halogens fluorine, chlorine, bromine and iodine.

As used herein, the term haloalkyl refers to a halo substituted alkyl, such as fluoroalkyl, chlorofluoroalkyl, bromochloroalkyl, bromofluoroalkyl, bromoalkyl, iodoalkyl, chloroalkyl and the like where the haloalkyl has one or more than one of the same or different halogens substituted for a hydrogen. Examples of haloalkyl include chlorodifluoromethyl, 1-chloroethyl, 2,2,2 trichloroethyl, 1,1 dichloroethyl, 2-chloro, 1,1,1,2 tetrafluoroethyl, bromoethyl and the like.

As used herein the term fluoroalkyl is a prefered subclass of haloalkyl, and refers to fluorinated and perfluorinated alkyl, for example fluoromethyl, difluoromethyl, trifluoromethyl, 2,2,2-trifluoroethyl, 1,2-difluoroethyl, 1,1,2,3-tetrafluorobutyl and the like.

The compounds of Formula I, are sufficiently basic to form acid addition salts and are useful both in the free base form and the form of acid-addition salts, and both forms are within the purview of the invention. The acid-addition salts are, in some cases, a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds can be prepared by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or by concentration of the solution or by any one of several other known methods. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC) or other art recognized means of monitoring organic reactions.

As described herein a noninteracting solvent can be N-methyl pyrrolidine (NMP), methylene chloride ($CH_2Cl_2$), tetrahydrofuran (THF), benzene or any other solvent that will not take part in the reaction. In a preferred method, the preparation of compounds of the invention is done in dried solvents under an inert atmosphere. Certain reagents used in example preparations are specified by abbreviation: triphenylphosphine (TPP), lithium aluminum hydride (LAH), triethylamine (TEA), diisopropylethylamine (DIPEA), and diethyl azodicarboxylate (DEAD). Ether is diethyl ether unless otherwise specified.

Compounds of Formula I may be prepared by several methods:

Compounds of Formula I can be prepared by the reaction of the appropriate hydroxy-Y-(Q) moiety and the appropriate $R_1$-$R_2$-$R_3$-phenol by the reaction described in U.S. Pat. No. 5,242,924, incorporated herein by reference.

Compounds of Formula I can be prepared by reaction of the appropriate $R_1$-$R_2$-$R_3$-phenol and the appropriate halo-Y-(Q) moiety as described in U.S. Pat. No. 4,942,241, incorporated herein by reference.

Compounds of formula I can be prepared by reacting a X-Y-O-[$R_1$-$R_2$-$R_3$-phenyl] compound (prepared from X-Y-hydroxy or X-Y-halo compounds and $R_1$-$R_2$-$R_3$-phenols by the methods described in U.S. Pat. Nos. 5,242,924 or 4,942,241) with a suitably functionalized Q compound. For example, a hydroxy Q compound, such as hydroxypyridine, can be reacted with halo-Y-O[$R_1$-$R_2$-$R_3$-phenyl] compound to form a compound of formula I. Likewise for example a halo pyridine can be reacted with a hydroxy-Y-O-[$R_1$-$R_2$-$R_3$-phenyl] compound to form a compound of formula I. Examples of known functionalized Q compounds are described in the examples, but any suitably functionalized Q compound, usable in known chemical reactions is contemplated.

Compounds of formula I wherein $R_3$ is phenyl or heterocyclyl can be preferably prepared by the reaction of a hydroxy-Y-(Q) moiety or halo-Y-(Q) moiety with a $R_1$-$R_2$-4-functionalized phenol by the methods described in U.S. Pat. Nos. 5,242,924 and 4,942,241, incorporated herein by reference. Then the functional group on the resulting 4-functionalized $R_1$-$R_2$-phenoxy-Y-Q compound is then substituted by or elaborated into the heterocyclyl or phenyl substituent $R_3$ as described in U.S. Pat. No. 5,051,437, incorporated herein by reference.

For example, in preparing compounds of formula I wherein $R_3$ is haloalkyl-substituted oxadiazolyl, or haloalkyl-substituted thiadiazolyl, it is preferred that the corresponding 4 functionalized-$R_1$-$R_2$-phenoxy-Y-(Q) species be prepared, and the $R_3$ heterocycle be elaborated in the final steps of the synthesis.

When $R_3$ is pyrimidyl, phenyl, pyridyl, furyl, thienyl, benzofuranyl and the like it is preferred that the heterocycle be attached to the phenyl moiety by standard coupling methods. For example, when $R_3$ is pyridyl, a pyr-Y-O-$R_1$-$R_2$-phenyl borate can be reacted with a halo pyridine, such as bromopyridine to afford the corresponding compound of formula I wherein $R_3$ is pyridyl.

This method is also applicable to preparing $R_1$-$R_2$-$R_3$-phenols, useful in the method described above for preparing compounds of formula I, but where Q-Y- is replaced by a suitable protecting group, which is cleaved to liberate the $R_1$-$R_2$-$R_3$-phenol.

The skilled practitioner will recognize that certain $R_3$, especially heterocycles with 2 or more hetero atoms such as oxazolyl, oxadiazolyl, tetrazolyl, triazolyl and the like, are more easily prepared by elaborating a functional group, such as cyano, acyl, amino and the like, at the 4-position of the phenyl ring; thus forming the heterocycle "in situ" rather than attaching it in the $R_3$ position.

For example, the compound of Formula I can also be prepared from an appropriate 4-functionalized phenoxy -Y-(Q) species (abbreviated ZO-$R_1$-$R_2$-4-functionalized phenyl wherein Z is Q-Y), wherein the 4-phenoxy position is substituted with the desired heterocycle precursor. For example, Q-Y-O-$R_1$-$R_2$-benzaldehydes, and 4-[Q-Y-O-$R_1$-$R_2$-benzonitriles are known in the art (cf. for example, Mamose et al., Chem. Pharm. Bull. 39 1440–1445) or can be prepared from known materials, using methods well known in the art. In a preferred method, especially where $R_3$ is a substituted heterocycle two or more heteroatoms, it is preferred that the $R_3$ heterocycle is elaborated as a last step in the synthesis of the compound of formula I, as described in allowed U.S. patent application Ser. No. 07/869,287, incorporated hereby by reference. Suitable functional groups for the 4-phenoxy position will depend upon the heterocycle sought in the final product. For example, where Het is 1,2,4-oxadiazolyl

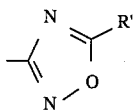

compounds are prepared from either the appropriate 4-Z-O-$R_1$-$R_2$-benzonitrile by reaction with hydroxylamine hydrochloride in a noninteracting solvent, preferably an alkanol, for example, methanol, ethanol, n-butanol and the like, in the presence of a base, such as potassium carbonate or pyridine, or in a preferred method, an alkali metal salt of a carboxylic acid such as sodium trifluoroacetate or sodium acetate, at a temperature between ambient temperature and the boiling point of the solvent. The product thus obtained is then reacted with an acid anhydride of formula (R'CO)$_2$O, (where R' is alkyl, haloalkyl); R appears as a substituent on the $R_3$heterocycle of the product. When R' is haloalkyl it is preferred that this reaction be the final synthetic step. Thus, the product is a compound of formula I, where the starting material is 4-ZO-$R_1$-$R_2$-benzonitrile and Z is Q-Y.

It will be understood that when Z represents a protecting group, the method will produce a protected phenol, which is deprotected to form an $R_1$-$R_2$-$R_3$-phenol. This phenol is then useful in preparing the compound of formula I when reacted with the appropriate hydroxy-Y-(Q) or halo-Y-(Q) as described above.

It will be appreciated that neither the timing of the elaboration of the heterocyclic substituents nor the order of assembly of the intermediates is crucial to the successful synthesis of compounds of Formula I. Thus by judicious choice of reactants one can prepare any of the compounds of Formula I, by several different routes.

The $R_1$-$R_2$-$R_3$-phenols (wherein $R_3$ is heterocyclyl) used to prepare compounds of Formula I are known in the art or prepared by known methods. For most phenols, their preparation is described in U.S. Pat. Nos. 4,942,241; 4,945,164; 5,051,437; 5,002,960; 5,110,821; 4,939,267; 4,861,971; 4,857,539; 5,242,924; or 4,843,087 incorporated herein by reference. In addition, other known phenols including, for example, 4-phenyl-$R_1$-$R_2$-phenols and 4-alkoxycarbonyl-$R_1$-$R_2$-phenols, are well known and can be used in preparing compounds of formula I. It is expected that any $R_1$-$R_2$-$R_3$-4-phenol disclosed in these patents, described elsewhere in the art, or prepared by methods known in the art are useful in preparing compounds of formula I.

$R_1$-$R_2$-$R_3$-phenols, ($R_3$=heterocycle) can be prepared from the suitably protected phenol which has been functionalized at the 4-position by a functional group such as cyanide, aldehyde, halide, acid chloride group or other suitable reactive group, by preparing the heterocycle "in situ" as described above or as described in U.S. Pat. Nos. 4,942,241; 4,945,164; 5,051,437; 5,002,960; 5,110,821; 4,939,267; 4,861,971; 4,857,539; 5,242,924; or 4,843,087 each incorporated herein by reference, or methods known in the literature. The heterocycle is elaborated from the functional group and the phenol is deprotected by means well known in the art. Alternatively, $R_1$-$R_2$-$R_3$-phenols may be prepared by displacing a functional group, e.g. halo, with the $R_3$ substituent as described above.

Hydroxy-Y-Q compounds can be prepared from known pyridine, pyrimidine or pyrazine halides, alcohols, acids or carboxyalkyl compounds or from any other known pyridines, pyrimidines or pyrazines that can be suitably functionalized by known methods. For a review of reaction methods, see Katritsky and Rees, *Comprehensive Heterocyclic Chemistry* volume 2 and 3 (Pergamon, 1984), especially sections 2.13–2.14.

For example, pyridinyl triflate can be reacted with a X-Y-Z compound where Z is a functional group, wherein Y has a terminal alkenyl or alkynyl linkage and X is a tin species such as tributyl tin. Other useful Y-Z species include terminally unsaturated acids, esters or alcohols, such as alkynyl alkanols, α,β-unsaturated esters and the like. It is preferred that alkanols and acids be suitably protected. After reaction the resulting unsaturated alkanols, esters and acids are reduced to alkanols and any unsaturation in the alkyl backbone may be partially or completely reduced by known methods. Such reduction methods include, but are not limited to palladium or carbon, lithium aluminum hydride or other hydride reduction. Alternatively, such alkanols may be prepared by reaction of pyridyl ketones, aldehydes and the like, for example under Wittig conditions, to yield the corresponding unsaturated esters and the like which can be reduced as described above. The hydroxy-Y-(Q) can be prepared from the known pyridyl, pyrimidyl or pyrazyl triflate or halide and an unsaturated species by palladium coupling, (such as the Heck reaction) which is well known in the art. Halo-Y(Q) compounds are prepared by analagous, known methods.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; alkylation of phenyl or other aromatic and heterocyclic substituents; cleavage of alkyl or benzyl ethers to produce the corresponding alcohols or phenols; and hydrolysis of esters or amides to produce the corresponding acids, alcohols or amines, preparation of anhydrides, acid halides, aldehydes, simple aromatic alkylation and the like as desired can be carried out.

Moreover, it will be appreciated that obtaining the desired product by some reactions will be better facilitated by blocking or rendering certain functional groups nonreactive. This practice is well recognized in the art, see for example, Theodora Greene, *Protective Groups in Organic Synthesis* (1991). Thus when reaction conditions are such that they can cause undesired reactions with other parts of the molecule, the skilled artisan will appreciate the need to protect these reactive regions of the molecule and act accordingly.

Starting materials used to prepare the compounds of Formula I are commercially available, known in the art, or prepared by known methods.

EXEMPLARY DISCLOSURE

For the purpose of naming substituents in Formula I, the phenyl ring of any compound of formula I shall be numbered;

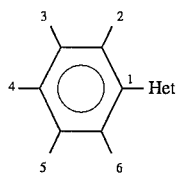

Thus when a compound of formula I has substitution on the phenyl ring, it is referred to by this numbering system regardless of how the compound is actually named. For example, if a compound is prepared and the designation $R_1,R_2$=3,5-dimethyl, this means

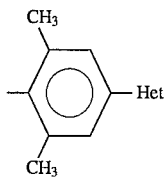

regardless of whether 3,5-dimethyl or 2,6-dimethyl appears the name of the compound.

PREPARATION OF INTERMEDIATES

Intermediate 1

A. Ethyl β-(6-methylpyridin-3-yl)acrylate

A suspension of 4.8 g of 6-methyl-3-pyridine-triflate, 2.5 g of LiCl, 4.3 ml of ethyl acrylate, and 0.32 g of $PdCl_2(P(Ph)_3)_2$ in 7.8 ml of triethylamine and 9.6 ml of dry DMF was heated at 100° C. under nitrogen for 36 h. The desired product was purified by flash chromatography on silica gel to afford 3.14 g (63%) of ethyl β-(6-methylpyridin-3-yl)acrylate, as a pale yellow-orange oil, B. Ethyl 3-(6-methylpyridin-3-yl)propionate A suspension of ethyl β-(6-methylpyridin-3-yl)acrylate (3.86 g, 20.2 mmol) in 200 ml of ethyl acetate and 1.4 g of 5.3% Pd/C was hydrogenated under hydrogen (50 psi) for 4 h. The mixture was filtered through SUPERCEL™, the filtrate was concentrated in vacuo to afford 3.75 g (96%) of ethyl 3-(6-methylpyridin-3-yl)propionate, as a pale orange oil.

C. 6-Methyl-3-(3-hydroxypropyl)pyridine

To a suspension of 0.75 g (1 equiv) of LAH in 50 ml of THF at 0° C. under nitrogen was added 3.75 g (19.4 mmol) of ethyl 3-(6-methylpyridin-3-yl)-propionate in 10 ml of THF. The reaction mixture was quenched, filtered, and the filtrate was concentrated in vacuo to yield 3.0 g of the product as a viscous red oil. The oil was filtered through florosil eluting with ethyl acetate and concentrated in vacuo to afford 2.5 g (86%) of 6-methyl-3-(3-hydroxypropyl)-pyridine as an orange oil.

Intermediate 2 a) 5.2 g (27 mmol) of 3-bromo-6-chloropyridine, 5.9 ml (Cl-Pyr-2 equivalents) of ethyl acrylate, 12.5 ml (2 equivalents) of tributyl amine and 0.176 g of palladium bis acetate were taken up in 10 ml DMF and heated to 100° C. for 24 hours. The reaction mixture was extracted with dilute HCl and then base. The organic fraction was then dried over magnesium sulfate, filtered and concentrated in vacuo to an oil, which was applied to silica gel and eluted with 0 3: 1 hexane/ethyl acetate, the product was recrystallized from hexane to give 2.3 g of pure product. Remaining residue was purified by chromatography and recrystallized from hexane to give an additional 2.0 g of product (68%) of the desired product.

b) A suspension of 0.84 g of Te powder, 0.60 g of $NaBH_4$ and 32 ml ethanol was heated under nitrogen until the reaction mixture became purple. To this solution was added 1.38 g of the product from 11a and the mixture was refluxed for 4 hours and upon cooling quenched with water. The reaction mixture was extracted with water and the organic fraction was then dried over magnesium sulfate, filtered and concentrated in vacuo to an oil, which was applied to silica gel and eluted with 3:1 hexane/ethyl acetate giving 1.11 g of product that was used in the next synthetic step without purification.

c) To a suspension of 0.2 g of lithium aluminum hydride in 25 ml of dry THF at 0° C was added the solution of 1.11 g of the product of preparation 2b (above) in 5 ml THF. The reaction was maintained at 3°–5° C. for 4 hours and then quenched with water and 10% NaOH, and filtered through celite while washing with ether. The organic fraction was concentrated in vacuo to afford 0.87 g of the 3 (6-chloro-3-pyridyl)propanol product as an oil, used without further purification.

Intermediate 3 a) A suspension of 5.0 g of 2-methyl-5-triflylpyridine, 2.62 g of lithium chloride 4.5 ml of ethyl acrylate and 8.2 ml of triethyl amine and 0.345 g of dichlorotdi(triphenyl)phosphinepalladium $(Pd(pH_3)_2Cl_2)$ in 10 ml dry DMF was heated to 100° C. for 36 hours. The suspension was then diluted with ethyl acetate and poured into water. The organic phase was washed thrice with water and dried over potassium carbonate. Concentration and flash chromatography on kieselgel with 3:2 hexane ethyl acetate provided 3.2 g (80%) of the desired product used without further purification.

b) A suspension of 3.2 g of the product of preparation 12a and 1.0 g of 53% palladium on carbon in 200 ml ethyl acetate was subjected to 50 psi hydrogen. Filtration and concentration yielded 3.1 g (97%) of the desired product as an orange oil, used in the next step without further purification.

c) A suspension of 0.62 g of lithium aluminum hydride on 50 ml of dry THF was cooled to 0° C. under nitrogen. To this suspension 3.1 g of the ester of preparation 3b (above) in 10 ml THF was added and stirred for an hour. The reaction was quenched with water and NaOH. The product was filtered through celite, and residue washed through with ethyl acetate. The product was dried, concentrated in vacuo, yeilding 2.4 g of the 3-(3-methyl)pyridyl)propanol.

Intermediate 4

Using any known or commercially available halide, of which the following are examples (while others are contemplated);

a) 4 pyridyl chloride
b) 2-methyl-4-pyridyl chloride
c) 5-methyl-2-pyridyl bromide
d) 4-methyl-2-pyridyl chloride
e) 2-pyridazyl chloride f) 2-bromo-6-methyl pyrimidine
g) 2-bromo-5-methyl pyrimidine
and ethyl acrylate one can prepare intermediates the following intermediate 3-(Pyr)propanols using the methods of Intermediate 2.
  a) 3-(4-pyridyl)propanol
  b) 3-(2-methyl-4-pyridyl)propanol
  c) 3-(5-methyl-2-pyridyl)propanol
  d) 3-(4-methyl-2-pyrimidyl)propanol
  e) 3-(2-pyridazyl)propanol
  f) 3-(6-methyl-2-pyridyl)propanol
  g) 3-(5-methyl-2-pyrimidyl)propanol Any of the above alkanols can be reacted with any of the phenols of Example 19, Intermediate 5, and the like using the method of Example 1E to afford compounds of formula I.

Intermediate 5

1.68 g (10 mmol) 3-fluoro-4-methoxyacetophenone and 4.88 g (11 mmol) lead tetraacetate were dissolved in 10 mL benzene and refluxed. Ethylene glycol was used to quench the reaction. On standing, the resulting 3.19 g of yellow oil crystallized. 1.44 g (6.37 mmol) of the crystals and 2.31 g (30 mmol) of ammonium acetate were combined in 15 mL glacial acetic acid and refluxed 4 hours. The product was poured into water, then basified. The aqueous layer was extracted twice with methylene chloride then concentrated to dryness and recrystallized from methylene chloride yielding 0.8 g of product, 0.59 g (2.85 mmol) of which was taken up in 25 mL methylene chloride and combined with 2 mL of a 1M solution of boron tribromide in methylene chloride and refluxed for 30 minutes. The product was poured into water and basified. The aqueous layer was washed twice with methylene chloride. The organic layers were combined and washed with water, 1N HCl, and brine and evaporated to dryness. The product was recrystallized from methanol giving 0.09 g of 4-(2-fluoro-4-hydroxyphenyl)-2-methyl-4-oxazole.

EXAMPLE 1

A. 2-Fluoro-5-bromopyridine

A suspension of 2.2 g (15.6 mmol) of 2-fluoro-5-pyridinecarboxylic acid, 5.1 g of HgO (red) and 1.2 ml of bromine in 100 ml of CCl$_4$ was irradiated (by) under reflux for 5 h, cooled to room temperature, filtered through celite, and the filtrate was concentrated in vacuo. The residue was dissolved in hexane, filtered, and the filtrate was concentrated in vacuo to afford 1.73 g (63%) of 2-fluoro-5-bromopyridine, as a pale yellow oil.

B. 2-Fluoro-5-[3-(t-butyl-dimethylsilyloxy)-2-propynyl]pyridine

A suspension of 1.45 g (8.2 mmol) of 2-fluoro-5-bromopyridine, 4.2 g (1.1 eq) of 1-tributyltin-3-t-butyl-dimethylsilyloxy-2-propyne and 0.11 g (3 mol %) of PdCl$_2$(P(Ph)$_3$)$_2$ in 5 ml of dry THF was refluxed under nitrogen for 24 h. The mixture was concentrated in vacuo and the residue was purified by flash filtration (silica gel; hexane/ethyl acetate, 3:1) and MPLC (26 id, silica gel 60, hexane/ethytl acetate, 5:1) to afford 2.3 g (2.2 g-theory) of 2-fluoro-5-[3-(t-butyl-dimethylsilyloxy)-2-propynyl]pyridine, as a dark red oil (crude).

C. 2-Fluoro-5-(3-t-butyl-dimethylsilyloxy)propyl-pyridine

A suspension of 1.5 g (5.7 mmol) of 2-fluoro-5-[3-(t-butyl-dimethylsilyloxy)-2-propynyl]pyridine and 0.58 g of 5% Pd/C in 200 ml of ethyl acetate was hydrogenated at 50 psi (H$_2$) for 2 h. The mixture was filtered and the filtrate was concentrated in vacuo to yield 2.1 g of a red oil (crude). The red oil was purified by MPLC (26 id, Kieselgel 60, hexane/ethyl acetate, 6:1) to afford 0.78 g (52%) of 2-fluoro-5-(3-t-butyl-dimethylsilyloxy)propyl-pyridine, as a light red oil.

D. 2-Fluoro-5-(3-hydroxy)propyl-pyridine

To a suspension of 0.78 g (2.9 mmol) of 2-fluoro-5-(3-t-butyldimethylsilyloxy)-propyl-pyridine in 10 ml of dry THF was added 3.8 ml (1.3 eq) of 1M TBAF solution in THF. The dark brown solution was stirred under nitrogen at room temperature for 2 h, poured into water and extracted with ether. The organic layer was washed with water, dried over sodium sulfate, filtered, and the filtrate was concentrated in vacuo to afford 0.26 g (57.8%) of 2-fluoro-5-(3-hydroxy)-propylpyridine, as a brown oil.

E. 2-Fluoro-5-[3-[4-(5-trifluoromethyl-1,2,4-oxadiazol-3-yl)-2,6-dimethylphenoxy]-propyl]-pyridine (I, Q=6-fluoro-3-pyridyl, Y=1,3-propylene, R$_1$, R$_2$=3,5-dimethyl, R$_3$=5-trifluoromethyl-1,2,4-oxadiazol-3-yl)

To a suspension of 0.31 g (1.2 mmol) of 4-(5-trifluoromethyl-1,2,4-oxadiazol-3-yl)-2, 6-dimethylphenol, 0.26 g (1.4 eq) of 2-fluoro-5-(3-hydroxypropyl)-pyridine, 0.45 g (1.4 eq) of triphenylphosphine in 40 ml of methylene chloride under nitrogen at 0° C. was added dropwise a solution of 0.28 g (1.4 eq) of DEAD in 2 ml of methylene chloride. The dark brown solution was stirred at room temperature for 24 h, concentrated in vacuo and the residue was purifed by MPLC (26 id Kieselgel 60 column; hexane/ethyl acetate 5:1) to yield 5.5 g of the product. Recrystallizations from t-butylmethylether/hexane as well as hexane (2nd recrystallization) afforded 0.23 g (48.9%) of 2-fluoro-5-[3-[4-(5-trifluoromethyl-1,2,4-oxadiazol-3-yl)-2,6-dimethylphenoxy]-propyl]-pyridine, as a white solid. The above product was repurified by preparative tlc (hexane/ethyl acetate/triethylamine, 5:1:0.5) to yield 0.22 g (46.8%) of a white solid.

EXAMPLE 2

A. 2-Chloro-5-bromopyridine

A suspension of 2 g (12 mmol) of 2-chloro-5-pyridinecarboxylic acid, 4.12 g (19 mmol) of HgO (red) and 1 ml (19 mmol) of bromine in CCl$_4$ was irradiated (flood lamp) under reflux for 2.5 h. The mixture was cooled to room temperature, 30 ml of sat. sodium bicarbonate solution was added, and the mixture was stirred vigorously for 15 min. The biphasic orange suspension was filtered through celite, the organic layer was washed with brine and dried over sodium sulfate. The filtrate was concentrated in vacuo to afford 1.1 g (45.8%) of 2-chloro-5-bromopyridine, as a white solid, m.p. 67°–69° C.

B. Ethyl β-(2-chloropyridin-5-yl)acrylate

A suspension of 0.5 g (2.6 mmol) of 2-chloro-5-bromopyridine, 1.2 ml (2 eq) of tri-n-butylamine, 0.56 ml (2 eq) of ethyl acrylate, and 17 mg (3 mol %) of Pd(OAc)$_2$ in 1 ml of dry DMF was heated at 80°–90° C. under nitrogen for 40 h. The mixture was poured into ether, washed with sat. ammonium chloride solution followed by water. The organic layer was dried over potassium carbonate and concentrated in vacuo to yield 1 g of a dark solid which was purified by preparative tlc (2000 micron silica gel –2 plates, hexane/ethyl acetate, 2:1) to afford 0.26 g (47.3%) of ethyl b-(2-chloropyridin-5-yl)acrylate, as a solid.

C. Ethyl 3-(2-chloropyridin-5-yl)propionate

A suspension of 0.84 g (1 eq) of Te powder and 0.6 g (2 eq) of NaBH$_4$ in 32 ml of ethanol was heated under nitrogen until it became a homogeneous purple solution. To the above hot solution was added ethyl β-(2-chloropyridin-5yl)acrylate (1.38 g, 6.5 mmol) and the mixture was refluxed for 4 h. The crude product was purified by flash chromatography (silica gel; hexane/ethyl acetate, 3:1) to afford 1.11 g (84,6%) of ethyl 3-(2-chloropyridin-5-yl)propionate.

D. 2-Chloro-5-(3-hydroxypropyl)pyridine

To a suspension of 0.2 g of LAH in 25 ml of dry THF at 0° C. under nitrogen was added a solution of 1.11 g (5.2 mmol) of ethyl 3-(2-chloropyridin-5-yl)-propionate in 5 ml of THF. The reaction mixture was kept at 3° C.–5° C. for 1 h and quenched with 0.2 ml of water, 0.2 ml of 10% NaOH, and 0.6 ml of water successively. The mixture was filtered through celite (washing with ether) and the filtrate was concentrated in vacuo to yield 0.87 g (theory) of 2-chloro-5-(3-hydroxypropyl)-pyridine as a yellow viscous oil (crude).

E. 2-Chloro-5-[3-[4-(5-trifluoromethyl-1,2,4-oxadiazol-3-yl)-2,6-dimethylphenoxy]-propyl]-pyridine (I, Q=6-chloro-3-pyridyl, Y=1,3-propylene, $R_1$, $R_2$=3,5-dimethyl, $R_3$=5-trifluoromethyl-1,2,4-oxadiazol-3-yl)

To a suspension of 1.12 g (4.34 mmol) of 4-(5-trifluoromethyl-1,2,4-oxadiazol-3-yl)-2,6-dimethylphenol, 0.87 g (1.2 eq) of 2-chloro-5-(3-hydroxypropyl)-pyridine, 1.4 g (1.2 eq) of triphenylphosphine in 50 ml of methylene chloride under nitrogen at 0° C. was added dropwise a solution of 0.86 g (1.2 eq) of DEAD in 5 ml of methylene chloride. The mixture was stirred under nitrogen at room temperature for 60 h, concentrated in vacuo and the residue was triturated with hexane/ethyl acetate, filtered, and the filtrate was concentrated in vacuo to yield a dark brown oil. The brown oil was purified by MPLC (50 id, Kieselgel 60 column, hexane/ethyl acetate, 3:1) to afford 1.4 g (78%) of 2-chloro-5-[3-[4-(5-trifluoromethyl-1,2,4-oxadiazol-3-yl)-2,6-dimethylphenoxy]-propyl]-pyridine, as a white crystalline solid, m.p. 89°–91° C.

EXAMPLE 3

A. 2-Methoxypyridine-5-carboxaldehyde

To a solution of 4.8 g (25.5 mmol) of 2-methoxy-5-bromopyridine in ether cooled to 0° C. was added 16.6 ml (1.1 eq) of t-butyllithium in pentane. The above reaction mixture was cooled to −78° C., 2.2 ml of DMF in ether was added and the resulting mixture was stirred at −78° C. and then allowed to warm to room temperature. The mixture was quenched with sat. aqueous ammonium chloride and diluted with water. The organic layer was separated, washed with water, dried over sodium sulfane, and concentrated in vacuo to yield 3.6 g of a yellow crude oil which was further purified by flash chromatography (silica gel 60, hexane/ethyl acetate, 3:1) to afford 2.54 g (71.2%) of 2-methoxypyridine-5-carboxaldehyde, as a pale yellow oil which solidified upon standing.

B. Methyl β-(2-methoxypyridin-5-yl)acrylate

A suspension of 0.65 g (1.1 eq) of 95% NaH in 22 ml of toluene was slowly added to 3.8 g (1 eq) of methyl diethylphosphonoacetate in 5 ml of dry toluene below 35° C. The clear yellow solution was allowed to stir under nitrogen at room temperature for 30 min and a solution of 2.5 g (18.2 mmol) of 2-methoxy-pyridine-5-carboxaldehyde in 10 ml of toluene was added dropwise while maintaining the reaction temperature below 40° C. After the addition, the mixture was heated at 65° C. for 30 min, cooled, and filtered through solka floc and concentrated in vacuo to yield 3 g (85.7%) of methyl β-(2-methoxypyridin-5-yl)acrylate (cis/trans mixture).

C. Methyl 3-(2-methoxypyridin-5-yl)propionate

A suspension of methyl β-(6-methoxypyridin-3-yl)acrylate (3 g, 15.5 mmol) and 1 g of 5% Pd/C in 100 ml of ethyl acetate was hydrogenated under hydrogen (50 psi). After hydrogen uptake had ceased, the mixture was filtered through solka floc, the filtrate was concentrated in vacuo to afford 2.7 g (90%) of methyl 3-(6-methoxypyridin-5-yl)propionate.

D. 2-Methoxy-5-(3-hydroxypropyl)pyridine

To a suspension of 0.56 g (1.1 eq) of LAH in 50 ml of dry THF at 5° C. under nitrogen was added a solution of 2.7 g (13.5 mmol) of methyl 3-(2-methoxy-pyridin-5-yl)-propionate in THF and the reaction mixture was stirred at room temperature for 2 h. The mixture was quenched with 0.6 ml of water, 0.6 ml of 10% NaOH, and 1.8 ml of water successively. The mixture was filtered and the filtrate was concentrated in vacuo to yield 2.0 g (87%) of 2-methoxy-5-(3-hydroxypropyl)-pyridine as a yellow oil.

E. 2-Methoxy-5-[3-[4-(5-methyl-1,2,4-oxadiazol-3-yl)-2,6-dimethylphenoxy]-propyl]-pyridine (I, Q=6-methoxy-3-pyridyl, Y=1,3-propylene, $R_1$,$R_2$=3,5-dimethyl, $R_3$=5-methyl-1,2,4-oxadiazol-3-yl)

To a suspension of 0.81 g (3.9 mmol) of 4-(5-methyl-1,2,4-oxadiazol-3-yl)-2,6-dimethylphenol, 0.8 g (1.2 eq) of 2-methoxy-5-(3-hydroxypropyl)-pyridine, 1.4 g (1.2 eq) of triphenylphosphine in 70 ml of methylene chloride under nitrogen at 5° C. was added in portions 0.88 g (1.2 eq) of DEAD. The mixture was concentrated in vacuo, the residue was triturated with ether, filtered, and the crude product was purified by MPLC (50 id, Kieselgel 60 column, hexane/ethyl acetate, 2:1) and recrystallization from isopropyl acetate/hexane to afford 1 g (71.4%) of 2-methoxy-5-[3-[4-(5-methyl-1,2,4-oxadiazol-3-yl)-2,6-dimethylphenoxy]-propyl]-pyridine, as a white powder, m.p. 71°–73° C.

F. 2-Methoxy-5-[3-[4-(5-trifluoromethyl-1,2,4-oxadiazol-3-yl)-2,6-dimethylphenoxy]-propyl]-pyridine (I, Q=6-methoxy-3-pyridyl, Y=1,3-propylene, $R_1$,$R_2$=3,5-dimethyl, $R_3$=5-trifluoromethyl-1,2,4-oxadiazol-3-yl)

To a suspension of 1.54 g (6 mmol) of 4-(5-trifluoromethyl-1,2,4-oxadiazol-3-yl)-2,6-dimethylphenol, 1.2 g (1.2 eq) of 2-methoxy-5-(3-hydroxypropyl)-pyridine, 1.9 g (1.2 eq) of triphenylphosphine in 50 ml of methylene chloride under nitrogen at 5° C. was added in portions 1.22 g (1.2 eq) of DEAD. The mixture was stirred at room temperature for 20 h, concentrated in vacuo, the residue was triturated with ether, and filtered. The crude product was purified by MPLC (50 id, Kreselgel 60 column, hexane/ethyl acetate, 3:1) to afford 2 g (82%) of 2-methoxy-5-[3-[4-(5-trifluoromethyl-1,2,4-oxadiazol-3-yl)-2,6-dimethylphenoxy]-propyl]-pyridine, as a clear oil, which upon recrystallization from isopropyl acetate/hexane afforded white powder, m.p. 62°–64° C.

G. 5-[3-[4-(5-Trifluoromethyl-1,2,4-oxadiazol-3-yl)-2,6-dimethylphenoxy]-propyl]-2(1H)-pyridone (I, Pyr=6-hydroxy-3-pyridyl, Y=1,3-propylene, $R_1$,$R_2$=3,5-dimethyl, $R_3$=5-trifluoromethyl-1,2,4-oxadiazol-3-yl)

A solution of 3.0 g (7.36 mmol) of 2-methoxy-5-[3-[4-(5-trifluoromethyl-1,2,4-oxadiazol-3-yl)-2,6-dimethylphenoxy]-propyl]-pyridine and 3.6 ml (3.4 eq) of trimethylsilyl iodide in 60 ml of 1,2-dichloroethane was refluxed under nitrogen for 1 h. The above red solution was quenched with methanol, poured into water, and diluted with methylene chloride. The organic layer was washed with sodium bisulfite, dried over magnesium sulfate, and concentrated in vacuo. The residue was recrystallized from isopropyl acetate to afford 1 g (34.5%) of 5-[3-[4-(5-trifluoromethyl-1,2,4-oxadiazol-3-yl)-2,6-dimethylphenoxy]-propyl]-2(1H)-pyridone, as a white, flaky solid, m.p. 128.5°–130.5° C.

H. 5-[3-[4-(5-Trifluoromethyl-1,2,4-oxadiazol-3-yl) -2,6-dimethylphenoxy]-propyl]-1-methyl-2-pyridone (I, Q=1-methyl-2-pyridone, Y=1,3-propylene, $R_1$,$R_2$=3,5-dimethyl, $R_3$=5-trifluoromethyl-1,2,4-oxadiazol-3-yl)

To a solution of 0.95 g (2.41 mmol) of 5-[3-[4-(5-trifluoromethyl-1,2,4-oxadiazol-3-yl)-2,6-dimethylphenoxy]-propyl]-2(1H)-pyridone, 20 drops of TDA-1, and 0.5 ml of methyl iodide in 50 ml of dry DMF was added 0.96 g (3 eq) of milled $K_2CO_3$. The mixture was filtered and concentrated in vacuo to afford 0.9 g (91.8%) of 5-[3-[4-

(5-trifluoromethyl-1,2,4-oxadiazol-3-yl)-2,6-dimethylphenoxy]-1-methyl-2-pyridone, as a white solid, which was recrystallized from isopropyl acetate to yield a white solid, 143°–146° C.

EXAMPLE 4

A. 2-Acetyl-6-(3-hydroxy-2-propynyl)pyridine

A suspension of 3 g (15.1 mmol) of 2-acetyl-6-bromopyridine, 0.89 g (15.9 mmol) of propargyl alcohol, 0.078 g of CuI, 300 mg of $PdCl_2(P(Ph)_3)_2$ in 60 ml of triethylamine was stirred under nitrogen at room temperature for 6 h. The mixture was diluted with water, extracted with ether, and the organic layer was washed with water (2x), brine, and dried over magnesium sulfate. The organic solution was concentrated in vacuo and the residue was purified by MPLC (silica gel 60, hexane/ethyl acetate, 1:1) to afford 1.3 g (50%) of 2-acetyl-6-(3-hydroxy-2-propynyl)pyridine, as a solid product.

B. 2-Acetyl-6-(3-hydroxypropyl)-pyridine

A suspension of 1.3 g of 2-acetyl-6-(3-hydroxy-2-propynyl)pyridine and 0.5 g of 10% Pd/C in 50 ml of ethyl acetate was hydrogenated at 50 psi ($H_2$) overnight. The mixture was filtered and the filtrate was concentrated in vacuo to yield 1.1 g (84.6%) of 2-acetyl-6-(3-hydroxypropyl)-pyridine, as a yellow oil (crude).

C. 2-Acetyl-6-[3-[4-(5-trifluoromethyl-1,2,4-oxadiazol-3-yl)-2,6-dimethylphenoxy]-propyl]-pyridine (I, Q=2-acetyl-2-pyridyl, Y=1,3-propylene, $R_1,R_2$=3,5-dimethyl, $R_3$=5-trifluoromethyl-1,2,4-oxadiazol-3-yl)

To a suspension of 0.1 g (0.55 mmol) of 2-acetyl-6-(3-hydroxypropyl)-pyridine, 0.14 g of 4-(5-trifluoromethyl-1,2,4-oxadiazol-3-yl)-2,6-dimethylphenol, 0.175 g (1.2 eq) of triphenylphosphine in DMF under nitrogen at 0° C. was added dropwise a solution of 0.097 g (1.2 eq) of DEAD in DMF. The bright red solution was stirred at room temperature overnight, diluted with water, and extracted with ethyl acetate. The organic layer was dried over magnesium sulfate, concentrated in vacuo, and the residue was purifed by MPLC to afford 2-acetyl-6-[3-[4-(5-trifluoromethyl-1,2,4-oxadiazol-3-yl)-2,6-dimethylphenoxy]-propyl]-pyridine.

EXAMPLE 5

A. 3-[4-(t-Butyl-dimethylsilyloxy)-2-butynyl]pyridine

A suspension of 2 g (12.6 mmol) of 3-bromopyridine, 8.4 g (17.8 mmol) of 1-tributyltin-4-t-butyl-dimethylsilyloxy-2-butyne and 40 mg of $PdCl_2(P(Ph)_3)_2$ in 5 ml of dry THF was refluxed under nitrogen. After adding additional 1-tributyltin-4-t-butyl-dimethylsilyloxy-2-butyne, the mixture was refluxed ovenight. The mixture was concentrated in vacuo and the residue was purified by flash filtration (2x; silica gel; hexane/ethyl acetate, 1/0, and 3:1) to afford 2.2 g (66.6%) of 3-[4-(t-butyl-dimethylsilyloxy)-2-butynyl]pyridine, as an amber oil.

B. 3-(4-t-Butyl-dimethylsilyloxy)butyl-pyridine

A suspension of 2.2 g (8.43 mmol) of 3-[4-(t-butyldimethylsilyloxy)-2-butynyl]pyrine and 2 g of 10% Pd/C in 50 ml of ethyl acetate was hydrogenated at 20 psi ($H_2$) for 2 h. The mixture was filtered through SUPERCEL™ and the filtrate was concentrated in vacuo to yield 2.1 g (52%) of 3-(4-t-butyl-dimethylsilyloxy)butyl-pyridine, as a solid product.

C. 3-(4-Hydroxy)butylpyridine

A solution of 2.13 g (7.6 mmol) of 3-(4-t-butyldimethylsilyloxy)butyl-pyridine in 50 ml of dry THF was added to 8.4 ml (2.2 eq) of 1M TBAF solution in THF. The solution was stirred under nitrogen at room temperature overnight. The mixture was diluted with water, extracted with ether, and the organic layer was washed with water, and dried over potassium carbonate. The organic layer was filtered, and the filtrate was concentrated in vacuo to afford 1.26 g of a yellow oil. The oil was dried in vacuo overnight to afford 0.25 g (21.7%) of 3-(4-hydroxy)-butylpyridine, as a yellow oil.

D. 3-[4-[4-(5-trifluoromethyl-1,2,4-oxadiazol-3-yl)-2,6-dimethylphenoxy]-butyl]-pyridine (I, Q=3-pyridyl, Y=1, 4-butylene, $R_1,R_2$=3,5-dimethyl, $R_3$=5-trifluoromethyl-1, 2,4-oxadiazol-3-yl)

To a suspension of 0.44 g (1.8 mmol) of 4-(5-trifluoromethyl-1,2,4-oxadiazol-3-yl)-2,6-dimethylphenol, 0.25 g (1.66 mmol) of 3-(4-hydroxybutyl)-pyridine, and 0.52 g (1.99 mmol) of triphenylphosphine in 30 ml of methylene chloride under nitrogen at 0° C. was added dropwise a solution of 0.35 g (1.97 mmol of DEAD in methylene chloride, and the resulting mixture was allowed to warm to room temperature. After adding 70 mg of triphenylphosphine, the mixture was stirred at room temperature for 2 days. The solution was concentrated in vacuo and the residue was purifed by MPLC (26 id Kieselgel 60 column; hexane/ethyl acetate 3:1) to yield 0.56 g (86.1%) of 3-[4-[4-(5-trifluoromethyl-1,2,4-oxadiazol-3-yl)-2,6-dimethylphenoxy]-butyl]-pyridine, as a pale yellow oil.

EXAMPLE 6

A. 3-(3-Hydroxypropyl)pyridine

3-Bromopyridine and ethyl acrylate were reacted as in example 1A giving the corresponding (3-pyridyl) α,β-unsaturated propionic ethyl ester which was then reduced with palladium on carbon with hydrogen and with lithium aluminum hydride to produce the corresponding 3-(3-pyridyl)-propanol.

B. 3-[3-[4-(5-Trifluoromethyl-1,2,4-oxadiazol-3-yl)-2,6-dimethylphenoxy]-propyl]-pyridine (I, Q=3-pyridyl, $R_1$, $R_2$=3,5-dimethyl, Y is 1,3-propylene, $Het_2$=5-trifluoromethyl-1,2,4-oxadiazol-3-yl)

The propanol from Example 7A was reacted with the phenol of Example 1D using triphenylphosphine and DEAD as in Example 1D to form a compound of formula I.

C. 3-[3-[4-(5-Trifluoromethyl-1,2,4-oxadiazol-3-yl)-2,6-dimethylphenoxy]-propyl]-pyridine-N-oxide (I, Q=3-pyridyl-N-oxide, Y=1,3-propylene, $R_1,R_2$=3,5-dimethyl, $R_3$=5-trifluoromethyl-1,2,4-oxadiazol-3-yl)

To a solution of 3-[3-[4-(5-trifluoromethyl-1,2,4-oxadiazol-3-yl)-2,6-dimethylphenoxy]-propyl]-pyridine (1 g, 2.6 mmol) in 50 ml of methylene chloride cooled to 0° C. was added 0.67 g (3.9 mmol) of m-chloroperoxybenzoic acid, and the mixture was allowed to stir overnight. The mixture was washed with saturated sodium bicarbonate, the organic layer was dried over magnesium sulfate and concentrated in vacuo to afford 1 g (98%) of 3-[3-[4-(5-trifluoromethyl-1, 2,4-oxadiazol-3-yl)-2,6-dimethylphenoxy]-propyl]-pyridine-N-oxide, as a yellow oil which crystallized (yellow flakes) on standing, m.p. 84°–86°C.

D. 1-Methyl-3-[3-[4-(5-trifluoromethyl-1,2,4-oxadiazol-3-yl)-2,6-dimethylphenoxy]-propyl]-pyridinium methanesulfonate (I, Pyr=1-methyl-3-pyridyl, Y=1,3-propylene, $R_1,R_2$=3,5-dimethyl, $R_3$=5-trifluoromethyl-1,2,4-oxadiazol-3-yl)

To a solution of 3-[3-[4-(5-trifluoromethyl-1,2,4-oxadiazol-3-yl)-2,6-dimethylphenoxy]-propyl]-pyridine (1 g, 2.6 mmol, 1.1 eq) in 10 ml of methylene chloride was added methyl methanesulfonate (0.32 g, 2.9 mmol) and the mixture was gently refluxed overnight. After adding 0.5 eq of methyl methanesulfonate, the mixture was allowed to reflux an additional 24 h. The mixture was concentrated in vacuo and a solid residue was washed with ether to afford 1.11 g (85.3%) of 1-methyl-3-[3-[4-(5-trifluoromethyl-1,2,4-oxadiazol-3-yl)-2,6-dimethylphenoxy]-propyl]-pyridinium methanesulfonate, as a white powder.

EXAMPLE 7

A. Ethyl β-(2-methylpyridin-3-yl)acrylate

A solution of 0.55 g (4.54 mmol) of 2-methylpyridine-5-carboxaldehyde in toluene was added dropwise into a cool suspension of 1.12 g (5 mmol) of ethyl diethylphosphonoacetate and 0.12 g (5 mmol) of NaH in toluene and the resulting solution was allowed to react at 65° C. for 30 min. After cooling, the mixture was filtered through SUPERCEL™ (wash SUPERCEL™ with ether) and concentrated in vacuo to yield 0.71 g (87.6%) of ethyl β-(2-methylpyridin-3-yl)acrylate (cis/trans mixture), which was further purified through a silica plug (hexane/ethyl acetate, 1:1).

B. Ethyl 3-(2-methylpyridin-3-yl)propionate

The compound from Example 8A was reduced with palladium on carbon and hydrogen to the corresponding ethyl ester according to the method of Example 1B.

C. 2-Methyl-3-(3-hydroxypropyl)pyridine

The α,β unsaturated ethyl ester from Example 8B was reduced using lithium aluminum hydride to the corresponding propanol using the method of Example 1C.

D. 3-[3-[4-(5-Trifluoromethyl-1,2,4-oxadiazol-3-yl)-2,6-dimethylphenoxy]-propyl]-2-methylpyridine (I, Q=2-methyl-3-pyridyl, Y=1,3-propylene, $R_1,R_2$=3,5-dimethyl, $R_3$=5-trifluoromethyl-1,2,4-oxadiazol-3-yl)

Propanol from Example 8C was reacted with the appropriate phenyl according to the method of example 1D to give a compound of Formula I.

EXAMPLE 8

A. 3-(3-Pyridyl)-propanol

The 3-(3-pyridyl)-propanol was prepared according to the method of Example 4A–D.

B. 3-[3-(2,6-dimethyl-4-cyanophenoxy)-propyl]-pyridine

The propanol from 9A was then reacted with 4-cyano-2,6-dimethyl-phenol according to the method of Example 1D.

C. 3-[3-(2,6-Dimethyl-4-aminohydroxyiminomethyl-phenoxy)-propyl]-pyridine

To a solution of 3.4 g (13 mmol) of 3-[3-(2,6-dimethyl-4-cyanophenoxy)-propyl]-pyridine with a small amount of dihydro-DEAD in 100 ml of ethanol was added at room temperature potassium carbonate (4.44 g; 64 mmol) and 8.21 g (64 mmol) of hydroxylamine hydrochloride, and the mixture was refluxed with stirring. The reaction mixture was cooled, filtered, the filtrate concentrated in vacuo to afford 3.9 g (theory) of 3-[3-(2,6-dimethyl-4-aminohydroxyimino-methylphenoxy)propyl]-pyridine.

D. 3-[3-[2,6-Dimethyl-4-(5-difluoromethyl-1,2,4-oxadiazol-2-yl-phenoxy)]-propyl]-pyridine (I, Q=3-pyridyl, Y=1,3-propylene, $R_1,R_2$=3,5-dimethyl, $R_3$=5-difluoromethyl-1,2,4-oxadiazol-3-yl)

A mixture of 3.9 g (13 mmol) of 2-[3-(2,6-dimethyl-4-aminohydroxyimino-methylphenoxy)propyl]-pyridine and 13 ml of ethyl difluoroacetate was refluxed for 2.5 h. The above reaction mixture was cooled, filtered, and the filtrate was concentrated in vacuo to yield 5 g of a crude residue. The residue was purified by silica gel chromatography (ethyl acetate/hexane, 2:1) and MPLC eluting with ethyl acetate/hexane (7:1) to afford 0.7 g (14.9%) of 3-[3-[2,6-dimethyl-4-(5-difluoromethyl-1,2,4-oxadiazol-2-yl-phenoxy)]propyl]-pyridine, as a white crystalline solid, m.p. 87°–89° C.

EXAMPLE 9

A. 3-(4-Pyridyl)-propanol 3-(4-Pyridyl)-propanol was prepared according to the method of 4A–D.

B. 4-[4-(5-Trifluoromethyl-1,2,4-oxadiazol-3-yl)-2,6-dimethylphenoxy]-propyl]-pyridine (I, Q=4-pyridyl, Y=1,3-propylene, $R_1,R_2$=3,5-dimethyl, $R_3$=5-trifluoromethyl-1,2,4-oxadiazol-3-yl)

To a suspension of 1 g (3.88 mmol) of 4-(5-trifluoromethyl-1,2,4-oxadiazol-3-yl)-2,6-dimethylphenol, 0.53 g (3.88 mmol) of 3-(4-pyridyl)-propanol, and 1.21 g (4.6 mmol) of triphenylphosphine in 10 ml of methylene chloride under nitrogen at 0° C. was added dropwise a solution of 0.81 g (4.6 mmol) of DEAD in methylene chloride, and the resulting mixture was allowed to warm to room temperature. The mixture was concentrated in vacuo and the residue was purifed by MPLC (hexane/ethyl acetate 1:3) to yield 1.5 g (86.1%) of 4-3-[4-(5-trifluoromethyl-1,2,4-oxadiazol-3-yl)-2,6-dimethylphenoxy]-propyl]-pyridine, as a white solid which was triturated in hexane, filtered, concentrated and recrystallized from isopropyl acetate/hexane to afford 0.82 g of a white solid.

EXAMPLE 10

C. 3-[3-[4-(5-Methyl-1,2,4-oxadiazol-3-yl)-2,6-dimethylphenoxy]propyl]-pyridine (I, Q=3-pyridyl, Y=1,3-propylene, $R_1,R_2$=3,5-dimethyl, $R_3$=5-methyl-1,2,4-oxadiazol-3-yl)

To a suspension of sodium hydride (70 mg, 2.8 mmol) and 3-hydroxypyridine (0.24 g, 2.56 mmol) in DMF was added dropwise 1 g (1 g, 2.8 mmol) of 4-(5-methyl-1,2,4-oxadiazol-3-yl)-2,6-dimethylphenoxypropyl iodide in DMF, and the mixture was stirred at room temperature for 2 days. The mixture was washed with water, extracted with ethyl acetate, and the organic layer was washed with water and dried over magnesium sulfate. The dry organic layer was concentrated in vacuo, passed through a pad of silica gel eluting with hexane/ethyl acetate (1:1) to afford 0.48 g (55.1%) of 3-[3-[4-(5-methyl-1,2,4-oxadiazol-3-yl)-2,6-dimethylphenoxy]propyl]-pyridine, as an oil, which crystallized on standing in ether, m.p. 46°–49° C.

EXAMPLE 11

A. 3-(4-Pyridyl)-propanol

The 3-(4-pyridyl)-propanol was prepared according to the method of 4A–D.

B. 4-[3-(2,6-Dimethyl-4-cyanophenoxy)-propyl]-pyridine 2,6-Dimethyl-4-cyanophenol was reacted with the alcohol of Example 12A according to the method of 1D.

C. 4-[3-(2,6-Dimethyl-4-aminohydroximinomethyl-phenoxy)-propyl]-pyridine

The amide oxime was formed from the cyano compound of Example 12B according to the method of 9C.

D. 4-[3-[2,6-Dimethyl-4-(5-difluoromethyl-1,2,4-oxadiazol-2-yl-phenoxy)]propyl]-pyridine (I, Q=4-pyridyl, Y=1,3-propylene, $R_1,R_2$=3,5-dimethyl, $R_3$=5-difluoromethyl-1,2,4-oxadiazol-3-yl)

A mixture of 1.15 g (3.6 mmol) of 4-[3-(2,6-dimethyl-4-aminohydroxyimino-methylphenoxy)propyl]-pyridine and 3.6 ml of ethyl difluoroacetate was heated at 100° C. for 6 h. The above reaction mixture was cooled, diluted with water, and extracted with ether. The organic layer was washed with water (5×100 ml), dried over magnesium sulfate and concentrated in vacuo to yield a residue. The residue was purified by silica gel pad chromatograph (ethyl acetate/hexane, 1:3) to afford 0.65 g (50%) of 4-[3-[2,6-dimethyl-4-(5-difluoromethyl-1,2,4-oxadiazol-2-yl-phenoxy)]propyl]-pyridine, m.p. 84°–86° C.

EXAMPLE 12

A. 2-Fluoro-6-(3-hydroxypropyl)pyridine

To a solution of 2-fluoro-6-methylpyridine (27 mmol) in 65 ml of freshly distilled THF was added via syringe 13.5 ml of 2M LDA, and the resulting mixture was stirred at −78° C. for 20 min. To the above cold solution was added 4 ml of 4M ethylene oxide and the mixture was allowed to warm to room temperature with stirring. The mixture was diluted with water, extracted with ether, and the organic layer was washed with water (2x) and brine, and dried over sodium sulfate. The organic solution was concentrated, and the residue was purified by flash chromatography (chloroform/ethanol, 10:1) to yield 1.3 g (30.9%) of 2-fluoro-6-(3-hydroxypropyl)pyridine, as a yellow oil.

B. 2-Fluoro-6-[4-(5-methyl-1,2,4-oxadiazol-3-yl)-2,6-dimethylphenoxy]-propyl]-pyridine (I, Q=6-fluoro-2-pyridyl, Y=1,3-propylene, $R_1,R_2$=3,5-dimethyl, $R_3$=5-methyl-1,2,4-oxadiazol-3-yl)

To a suspension of 0.66 g (3.22 mmol) of 4-(5-methyl-1,2,4-oxadiazol-3-yl)-2,6-dimethylphenol, 0.5 g (3.2 mmol) of 3-(2-fluoro-4-pyridyl)-propanol, and 1.27 g (4.83 mmol) of triphenylphosphine in 25 ml of methylene chloride under nitrogen at 0° C. was added dropwise a solution of 0.84 g (4.83 mmol) of DEAD in methylene chloride, and the resulting mixture was allowed to warm to room temperature. The mixture was concentrated in vacuo and the residue was purifed by silica plug chromatography and MPLC (hexane/ethyl acetate, 3:1) to afford 0.61 g (55.5%) of 2-fluoro-6-[4-(5-methyl-1,2,4-oxadiazol-3-yl)-2,6-dimethylphenoxy]-propyl]-pyridine, as a pale oil, which crystallized from t-butylmethyl ether, m.p. 54°–56° C.

EXAMPLE 13

Following the procedures described above in examples 1–13 the following compounds were prepared from known starting materials.

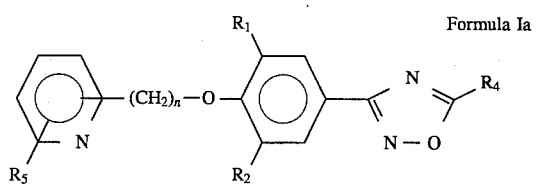

Formula Ia $Y=(CH_2)n$; $Q=m-(R_3$-pyridyl); $R_3$=5-$R_4$ 1,2,4-oxadiazolyl; $R_1=R_2$

| Ex. | $R_5$ | m = | $R_1$ | n | $R_4$ | m.p.(°C.) |
|---|---|---|---|---|---|---|
| 13a | H | 3 | $CH_3$ | 3 | $CH_3$ | 52–54 |
| 13b | H | 3 | $CH_3$ | 3 | $CF_3$ | 97–100 |
| 13c | H | 3 | Cl | 3 | $CH_3$ | 70–74 |
| 13d | H | 3 | Cl | 3 | $CF_3$ | 66–69 |
| 13e | 6-$CH_3$ | 3 | $CH_3$ | 3 | $CH_3$ | — |
| 13f | 6-$CH_3$ | 3 | $CF_3$ | 3 | $CF_3$ | 67–69 |
| 13g | H | 3 | $CH_3$ | 3 | $CF_2H$ | 87–89 |
| 13h | 2-$CH_3$ | 3 | $CH_3$ | 3 | $CF_2H$ | 67–69 |
| 13i | H | 3 | $CH_3$ | 4 | $CF_3$ | oil |
| 13j | 6-F | 2 | $CH_3$ | 3 | $CH_3$ | 54–56 |
| 13k | 2-$CH_3$ | 3 | $CH_3$ | 3 | $CF_3$ | 68–70 |
| 13l | H | 2 | $CH_3$ | 3 | $CF_3$ | 84–87 |
| 13m | N-oxide | 3 | $CH_3$ | 3 | $CF_3$ | 84–86 |
| 13n | 6-CN | 3 | $CH_3$ | 3 | $CF_3$ | 131–133 |

EXAMPLE 14

Using the methods described above, compounds of formula I wherein $R_3$ is 2-methyl-tetrazol-5-yl, Y is of the formula $(CH_2)_n$ and $R_1$ and $R_2$ represent 3,5-dimethyl were prepared by reaction of the appropriate pyridyl alkanol, pyridylalkylhalide of pyridylalkylsilane with 2-methyl-(4-hydroxy-3,5-dimethylphenyl)-2H-tetrazole.

| Ex | Y = | Pyr = | M.P. |
|---|---|---|---|
| 14a | —$(CH_2)_5$— | 2-pyridyl | 50–52 |
| 14b | C=C$(CH_2)_3$— | 3-pyridyl | 80–82 |
| 14c | $(CH_2)_5$ | 3-pyridyl | 43–44 |
| 14d | $(CH_2)_3$ | 4-pyridyl | 99–106 |
| 14e | $(CH_2)_3$ | 3-pyridyl | 64.5–66 |
| 14f | $(CH_2)_3$ | 6-methyl-3-pyridyl | 72–74 |
| 14g | $(CH_2)_3$ | 6-ethyl-3-pyridyl | 48–50 |
| 14h | $(CH_2)_5$ | 4-pyridyl | 64–66 |
| 14i | $(CH_2)_3$ | 3-methyl-4-pyridyl | 74–76 |
| 14j | $(CH_2)_3$ | 3-ethyl-4-pyridyl | 49–51 |
| 14k | $(CH_2)_3$ | 5-methyl-3-pyridyl | 76–77 |

EXAMPLE 15

Compounds of formula I wherein $R_1$, $R_2$=3,5-dimethyl and Y is 1,3-propylene were prepared by methods described hereinabove.

| Ex | Pyr = | $R_3$ = | M.P. |
|---|---|---|---|
| a | 4-pyrimidyl | 2-methyl-tetrazol-5-yl | 65–66 |
| b | 6-methyl-4-pyrimidyl | 2-methyl-tetrazol-5-yl | 78–79 |
| c | 6-methyl-4-pyrimidyl | 2-methyl-tetrazol-5-yl | 50–52 |
| d | 2-methyl-5-pyrimidyl | 5-trifluoromethyl-1,2,4-oxadiazol-3yl | 103–104 |
| e | 2-methyl-5-pyrimidyl | 5-methyl-1,2,4-oxadiazolyl | 94–96 |
| f | 2-methyl-5-pyrimidyl | 2-methyl-tetrazol-5-yl | 89–91 |

EXAMPLE 16

A  Ethyl 3-(3-quinolyl)propionate

A mixture of ethyl β-(3-quinolyl)acrylate (100 mg, 0.44 mmol) and 50 mg of 10% Pd/C in ethyl acetate/ethanol (3 ml/1 ml) was hydrogenated under hydrogen (55 psi) for 1 h. The mixture was filtered through celite, the residue was washed with methylene chloride, and the combined organic layer was concentrated in vacuo. Upon chromatographic purification on 20 cm silica column (ethyl acetate/hexane, 1/8-1/2), 49 mg (50%) of ethyl 3-(3-quinolyl)propionate (KUO-1953-136B) and 27 mg (26%) of ethyl 3-(1,2,3,4-tetrahydro-3-quinolyl)propionate was isolated.

B  3-(3-Hydroxypropyl)quinoline

To a cooled (0° C.) solution of ethyl 3-(3quinolyl)propionate (1.01 g, 4.4 mmol) in 20 ml of ether was added 2.6 ml (2.6 mmol) of 1M LAH solution at 0° C. After stirring at 0° C. for 15 min, the mixture was allowed to warm and stirred at 20° C. for 3 h, and Rochelle salt (equiv) was added. The mixture was extracted with methylene chloride, and the organic layer was dried over sodium sulfate, and concentrated in vacuo. The residue was purified by chromatography on silica (10 cm column, ethyl acetete/hexane, 1/2-5/1; methylene chloride/acetone, 2/1-1/4) to afford 700 mg (85%) of 3-(3-hydroxypropyl)quinoline, as a thick oil.

C  3-[3-[4-(5-Trifluoromethyl-1,2,4-oxadiazol-3-yl)-2,6-dimethylphenoxy]-propyl]-quinoline (I, Q=3-quinolyl Y=1,3-propylene, $R_1,R_2$=3,5-dimethyl, $R_3$=5-trifluoromethyl-1,2,4-oxadiazol-3-yl)

A mixture of 3-(3-hydroxypropyl)-quinoline (79 mg, 0.42 mmol), 4-(5-trifluoro-methyl-1,2,4-oxadiazol-3-yl)-2,6-dimethylphenol (119 mg, 0.46 mmol), and DEAD (80 mg, 0.46 mmol) was dissolved in 4 ml of THF. To the above solution was added triphenylphosphine (120 mg, 0.46 mmol) at 0° C. and the mixture was allowed to warm to 20° C. overnight. The solvent was removed in vacuo, and the residue was partitioned between an aqueous sodium bicarbonate solution and methylene chloride. The aqueous layer was extracted with methylene chloride (3x), and the organic layer dried over sodium sulfate and concentrated in vacuo. The residue was purified by silica column chromatography (20 cm column, ethyl acetate/hexane, 1/5 ) to afford 110 mg (96%) of 3-[3-[4-(5-trifluoromethyl-1,2,4-oxadiazol-3-yl)-2,6-dimethylphenoxy]-propyl]-quinoline.

D  3-[3-[4-(5-Methyl-1,2,4-oxadiazol-3-yl)-2,6-dimethylphenoxy]-propyl]-quinoline (I, Q=3-quinolyl, Y=1,3-propylene, $R_1,R_2$=3,5-dimethyl, $R_3$=5-methyl-1,2,4-oxadiazol-3-yl)

A mixture of 3-(3-hydroxypropyl)-quinoline (250 mg, 1.34 mmol), 4-(5-methyl-1,2,4-oxadiazol-3-yl)-2,6-dimethylphenol (273 mg, 1.34 mmol), and DEAD (256 mg, 1.47 mmol) was dissolved in 12 ml of THF. To the above solution was added triphenylphosphine (385 mg, 1.47 mmol) at 20° C. and the mixture was stirred overnight. The solvent was removed in vacuo, and the residue was partitioned between an aqueous sodium bicarbonate solution and methylene chloride. The aqueous layer was extracted with methylene chloride (3x), and the organic layer dried over sodium sulfate and concentrated in vacuo. The residue was purified by silica column chromatography (20 cm column, ethyl acetate/hexane, from 1/5 to 1/3) to afford 364 mg (73%) of 3-[3-[4-(5-methyl-1,2,4-oxadiazol-3-yl)-2,6-dimethylphenoxy]-propyl]-quinoline, m.p. 105°–107° C.

EXAMPLE 17

A  2-[3-[4-(2-Methyl-tetrazol-5-yl)-2,6-dimethylphenoxy]-propyl]-dioxalane

To a mixture of 4-(2-methyl-tetrazol-5-yl)-2,6-dimethylphenol (17 g, 83.2 mmol), 170 ml of NMP, potassium carbonate (11.5 g, 83.2 mmol), and 13.8 g (83.2 mmol) of potassium iodide was added 2-(3-chloropropyl)-1,3-dioxalane (11.42 g, 75.6 mmol) dropwise over a 10 min period, and the mixture was stirred at 90° C. overnight. After cooling, the mixture was poured into 900 ml of water and extracted with ether (4×250 ml) . The combined organic layer was washed with 10% NaOH solution, brine (170 ml), and dried over sodium sulfate and filtered. The organic filtrate was concentrated in vacuo, and the residue was purified by recrystallization from methylene chloride/hexane to afford 14.2 g (59%) of 2-[3-[4-(2-methyl-tetrazol-5-yl)-2,6-dimethylphenoxy]-propyl]-dioxalane, as a light pink solid, m.p. 84°–86° C.

B  4-[4-(2-Methyl-tetrazol-5-yl)-2,6-dimethylphenoxy]-butyraldehyde

2-[3-[4-(2-Methyl-tetrazol-5-yl)-2,6-dimethylphenoxy] propyl]-dioxalane (1 g, 3.1 mmol) was dissolved in 10 ml of acetic acid and 1 ml of water, and the mixture was stirred at 80° C. for 20 h. The solution was basified with 2N NaOH solution, extracted with methylene chloride, and the combined organic layer was dried over sodium sulfate and concentrated (with a crude product from KUO-1376-037) to afford 1.37 g of 4-[4-(2-methyl-tetrazol-5-yl)-2,6-dimethylphenoxy]butyr-aldehyde.

C  2-[4-[4-(2-Methyl-tetrazol-5-yl)-2,6-dimethylphenoxy]-1-hydroxy-butyl]-7-azaindole (Q=7-azaindol-2-yl, Y=1,4-butylene, $R_1$, $R_2$=3,5-dimethyl, $R_3$=2-methyltetrazol-5-yl)

To a cold solution of 1-phenylsulfonyl-7-azaindole (1.29 g, 5 mmol) in 250 ml of THF was added at −30° C. n-BuLi (2.5M in hexane, 4 ml, 10 mmol). The mixture was stirred at −30°–40° C. for 1 h and then cooled to −50° C. To the above mixture was added dropwise at −50° C. a solution of 4-[4-(2-methyl-tetrazol-5-yl)-2,6-dimethylphenoxy]butyraldehyde (1.37 g, 5 mmol) in 25 ml of THF, and the mixture was stirred at −40°–50° C. for 1 h and then allowed to warm to −5° C. for 2 h. Water was added to the mixture, and the resulting reaction mixture was acidified with 1N HCl solution, and then re-basified with an aqueous sodium bicarbonate solution, extracted with methylene chloride, and the organic layer was dried over sodium sulfate and concentrated in vacuo. The residue was purified by silica column chromatography (20 cm column, ethyl acetate/hexane, 1/5-1/0; then methylene chloride/acetone 2/1-1/1) followed by recrystallization from methylene chloride/methanol to afford 501 mg (25%) of 2-[4-[4-(2-methyl-tetrazol-5-yl)-2,6-dimethylphenoxy]-1-hydroxy-butyl]-7-azaindole, as a white crystalline solid, m.p.166°–169° C.

D  2-[4-[4-(2-Methyl-tetrazol-5-yl)-2,6-dimethylphenoxy]-butyl]-7-azaindole (I, Q=7-azaindol-2-yl, Y=1,4-butylene, $R_1$, $R_2$=3,5-dimethyl, $R_3$=2-methyl-tetrazol-5-yl)

Triethylsilane (5 ml) was added to a stirred solution of 2-[4-[4-(2-methyl-tetrazol-5-yl)-2,6-dimethylphenoxy]-1-hydroxy-butyl]-7-azaindole (520 mg, 1.33 mmol) in 20 ml of trifluoroacetic acid at 20° C. under nitrogen. The mixture was stirred at 20° C. for 10 min and then stirred at 70°–75° C. for 16 h. To the mixture was added water, and basified with an aqueous sodium bicarbonate solution (to pH=8) followed by extraction with methylene chloride (3x). The combined organic layer was dried over sodium sulfate and concentrated in vacuo. The residue was purified by silica column chromatography (7.5 cm column, ethyl acetate/hexane, 1/5-8/1) . The mixture was recrystallized to afford 349 mg (74%) of 2-[4-[4-(2-methyl-tetrazol-5-yl)-2,6-dimethylphenoxy]-butyl]-7-azaindole, as a white solid, m.p. 147°–150° C.

E  1-Methyl-2-[4-[4-(2-methyl-tetrazol-5-yl)-2,6-dimethylphenoxy]-butyl]-7-azaindole (I, Q=1-methyl-7-azaindol-2-yl, Y=1,4-butylene, $R_1$, $R_2$=3,5-dimethyl, $R_3$=2-methyl-tetrazol-5-yl)

To 150 ml of condensed liquid ammonia was added a trace of ferric nitrate. To the mixture sodium (69 mg, 3 mmol) was slowly added while removing a cold bath. A dark blue solution turned to a black-brown color. To the above solution was added slowly 2-[4-[4-(2-methyl-tetrazol-5-yl)-2,6-dimethylphenoxy]-butyl]-7-azaindole (376 mg, 1 mmol) in 7.5 ml of THF at −78° C. Methyl iodide (426 mg, 3 mmol) was added to the mixture at −78° C. and the resulting mixture was stirred at −78° C. for 30 min and then was allowed to warm to 20° C. over a 1 h period. The mixture was diluted with water, extracted with methylene chloride, and the organic layer was dried over sodium sulfate and concentrated in vacuo. The residue was purified by silica column chromatography (10 cm column, ethyl acetate/hexane, 1/5 -4/1) to yield 313 mg (71%) of a solid product which was recrystallized from methylene chloride/hexane to afford 273 mg of 1-methyl-2-[4-[4-(2-methyl-tetrazol-5-yl)-2,6-dimethylphenoxy]-butyl]-7-azaindole, 117.5°–119.5° C.

F  1-Methyl-2-[4-[4-(2-methyl-tetrazol-5-yl)-2,6-dimethylphenoxy]-butyl]-1,2-dihydro-7-azaindole (I, Q=2,3-dihydro-1-methyl-7-azaindol-2-yl, Y=1,4-butylene, $R_1$, $R_2$=3,5-dimethyl, $R_3$=2-methyl-tetrazol-5-yl)

A solution of 1-methyl-2-[4-[4-(2-methyl-tetrazol-5-yl)-2,6-dimethylphenoxy]-butyl]-7-azaindole (580 mg, 1.49 mmol) in 16.5 ml of trifluoroacetic acid was added in portions at 0° C. 1.88 g (29.7 mmol) of sodium borohydride. The mixture was stirred at 20° C. for 30 min and then heated at 55°–60° C. for 72 h. To the above mixture was added water, 2N NaOH solution (to pH=8), and the resulting mixture was extracted with methylene chloride. The organic layer was dried over sodium sulfate and concentrated in vacuo. The residue was purified by silica column chromatography (10 cm column, methylene chloride/acetone, 30/1-6/1) to yield 193 mg (33%) of 1-methyl-2-[4-[4-(2-methyl-tetrazol-5-yl)-2,6-dimethylphenoxy]-butyl]-2,3-dihydro-7-azaindole, as a solid, m.p. 54°–57° C.

G. Using the methods described above, compound of formula I wherein Q=2,3-dihydro-1-methyl-7-azaindolyl, Y=1,4-butylene, $R_1$, $R_2$=3,5-dimethyl and $R_3$ is 2-ethyl-tetrazol-5-yl; M.P. 75°–77° C.

EXAMPLE 18

A. 6-Methyl-3-[3-[4-(5-trifluoromethyl-1,2,4-oxadiazol-3-yl)-2,6-dimethylphenoxy]-propyl]-pyridine I, Q=6-methyl-3-pyridyl, Y=1,3-propylene, $R_1$,$R_2$=3,5-dimethyl, $R_3$=5-trifluoromethyl-1,2,4-oxadiazol-3-yl)

To a solution of 3.6 g (14 mmol) of 4-(5-trifluoromethyl-1,2,4-oxadiazol-3-yl)-2,6-dimethylphenol, 2.5 g (2 eq) of 6-methyl-3-(3-hydroxypropyl)-pyridine, (Int. 1C) 4.5 g (1.2 eq) of triphenylphosphine in 60 ml of methylene chloride under nitrogen at 0° C. was added dropwise a solution of 2.8 g (1.2 eq) of DEAD in 5 ml of methylene chloride. After 16 h, the mixture was concentrated in vacuo and the residue was purifed by MPLC (50 mm id Kieselgel 60 column; hexane/ethyl acetate 1:1) to yield 5.5 g of the product. Recrystallizations from t-butylmethylether/hexane as well as hexane (2nd recrystallization) afforded 2.88 g (52%) of 6-methyl-3-[3-[4-(5-trifluoromethyl-1,2,4-oxadiazol-3-yl)-2,6-dimethylphenoxy]-propyl]-pyridine.

B. 6-Methyl-3-[3-[4-(5-trifluoromethyl-1,2,4-oxadiazol-3-yl)-2,6-dimethylphenoxy]-propyl]-pyridine-N-oxide (I, Q=6-methyl-3-pyridyl-N-oxide, Y=1,3-propylene, $R_1$,$R_2$=3,5-dimethyl, $R_3$=5-trifluoromethyl-1,2,4-oxadiazol-3-yl)

To a solution of 1.08 g (2.8 mmol) of 6-methyl-3-[3-[4-(5-trifluoromethyl-1,2,4-oxadiazol-3-yl)-2,6-dimethytphenoxy]propyl]-pyridine in 30 ml of methylene chloride was added 0.71 g (1.5 eq) of m-chloroperbenzoic acid (MCPBA). The mixture was stirred under nitrogen for 18 h at room temperature, poured into saturated sodium bicarbonate solution, and the organic layer was separated and dried over sodium sulfate. The organic layer was fitered, concentrated, and the residue was recrystallized from isopropyl acetate/hexane to afford 0.93 g (83%) of 6-methyl-3-[3-[4-(5-trifluoromethyl-1,2,4-oxadiazol-3-yl)-2,6-dimethylphenoxy]-propyl]-pyridine-N-oxide, as white needles, m.p. 119°–121° C.

C. 6-Chloromethyl-3-[3-[4-(5-trifluoromethyl-1,2,4-oxadiazol-3-yl)-2,6-dimethylphenoxy]-propyl]-pyridine (I, Q=6-chloromethyl-3-pyridyl, Y=1,3-propylene, $R_1$,$R_2$=3,5-dimethyl, $R_3$=5-trifluoromethyl-1,2,4-oxadiazol-3-yl)

To a solution of 1.8 g (4.4 mmol) of 6-methyl-3-[3-[4-(5-trifluoromethyl-1,2,4-oxadiazol-3-yl)-2,6-dimethylphenoxy]-propyl]-pyridine-N-oxide in 18 ml of methylene chloride was added dropwise a solution of 0.41 ml (1.13 eq) $POC_{13}$ in 4 ml of methylene chloride. After addition of 10% of $POC_{13}$ solution, triethylamine (0.54 ml; 1.1 eq) in 4 ml of methylene chloride was added in portions. The exothermic mixture was stirred for 30 min, washed with saturated ammonium chloride solution, and the organic layer was separated and dried over sodium sulfate. The organic layer was concentrated in vacuo and purified by flash filtration through silica gel (hexane/ether, 2:1) to afford 0.59 g (31%) of 6-chloromethyl-3-[3-[4-(5-trifluoromethyl-1,2,4-oxadiazol-3-yl)-2,6-dimethyl-phenoxy]-propyl]-pyridine (BIL-1991-187), as a pale yellow oil which solidified upon standing, m.p. 79°–81° C.

D. 6-Methoxymethyl-3-[3-[4-(5-trifluoromethyl-1,2,4-oxadiazol-3-yl)-2,6-dimethylphenoxy]-propyl]-pyridine (I, Q=6-methoxymethyl-3-pyridyl, Y=1,3-propylene, $R_1$,$R_2$=3,5-dimethyl, $R_3$=5-trifluoromethyl-1,2,4-oxadiazol-3-yl)

To a solution of NaOMe in methanol (15 mg, 1 eq of 95% of NaH) was added 0.24 g (0.56 mmol) of 6-chloromethyl-3-[3-[4-(5-trifluoromethyl-1,2,4-oxadiazol-3-yl)-2,6-dimethyl-phenyl-phenoxy]-propyl]-pyridine. The suspension was brought to reflux thereby all solid dissolved and a mixture was allowed to cool to room temperature under nitrogen. The reaction mixture was allowed to reflux under nitrogen for 8 h. Upon cooling the mixture was diluted with ethyl acetate, the organic layer was washed with sat. ammonium chloride solution, dried over sodium sulfate, and concentrated in vacuo to yield 0.17 g of an orange semisolid. The solid was purified by preparative tlc (2000 micron silica gel; hexane/ethyl acetate, 3:2) to afford 0.1 g (41.7%) of 6-methoxymethyl-3-[3-[4-(5-trifluoromethyl-1,2,4-oxadiazol-3-yl)-2,6-dimethylphenoxy]-propyl]-pyridine as a colorless oil which solidified upon cooling in vacuo, m.p. 50°–53° C.

E. 6-Hydroxymethyl-3-[3-[4-(5-trifluoromethyl-1,2,4-oxadiazol-3-yl)-2,6-dimethylphenoxy]-propyl]-pyridine (I, Q=6-hydroxymethyl-3-pyridyl, Y=1,3-propylene, $R_1$,$R_2$=3,5-dimethyl, $R_3$=5-trifluoromethyl-1,2,4-oxadiazol-3-yl)

To a solution of 0.21 g (0.49 mmol) of 6-chloromethyl-3-[3-[4-(5-trifluoromethyl-1,2,4-oxadiazol-3-yl)-2,6-dimethylphenoxy]-propyl]-pyridine in 8 ml of DMF (dry, 3 A° sieves) under nitrogen at room temperature was added 0.12 g (1.1 eq) of AgTFA and the mixture was stirred under nitrogen for 20 h. The mixture was filtered through celite eluting with ethyl acetate, the organic layer was washed with water (4x), dried over sodium sulfate and concentrated in vacuo to yield 0.22 g of a pink oil (a mixture of starting material and the product, 2:1). The oil was resubjected to the reaction condition (0.2 g of AgTFA) stirring for 3 days followed by an addition of 0.1 g of AgTFA and stirring for 24 h at room temperature. The mixture was filtered through celite eluting with ethyl acetate, the organic layer was washed with water, dried over sodium sulfate and concentrated in vacuo to yield 0.17 g of a pink oil. The pink oil was dissolved in 10 ml of methanol and 10 drops of diethylamine, stirred for 1.5 h, and concentrated. The residue was purified by preparative tlc (2000 micron silica gel; chloroform/ethanol, 10:1) followed by recrystallization from isopropyl acetate/hexane to afford 1 mg (45.5%) of 6-hydroxymethyl-3-[3-[4-(5-trifluoromethyl-1,2,4-oxadiazol-3-yl)-2,6-dimethylphenoxy]-propyl]-pyridine, as a white soilid, m.p. 92°–94° C.

EXAMPLE 19

As further examples, phenols described only generally thus far can be reacted with any (Q)alkanol or (Q)alkyl halide described above using the methods previously described to provide a compound of compound of formula I. For the reader's convenience the same nomenclature conventions described herein for compounds of formula I are adhered to, and a literature reference describing the known phenol is included.

| $R_1$ | $R_2$ | $R_3$ | Reference U.S. Pat. Nos. |
|---|---|---|---|
| H | H | 1,2,4-oxadiazol-2yl | 4,857,539 |
| H | H | 4,2-dimethyl-2-thiazolyl | 4,857,539 |
| H | H | 2-benzoxazolyl | 4,857,539 |
| 3,5 dichloro | | 3-furanyl | 4,857,539 |
| 3,5 dichloro | | 2-furanyl | 4,857,539 |
| 3,5 dichloro | | 2-thienyl | 4,857,539 |
| 3,5 dichloro | | 2-pyridinyl | 4,857,539 |
| 3,5 dichloro | | 1-methyl-1H-pyrrol-2yl | 4,857,539 |
| 3,5 dichloro | | 3-thienyl | 4,857,539 |
| 3,5 dichloro | | 4-pyridinyl | 4,857,539 |
| 3 nitro | H | benzothiazol-2-yl | 4,857,539 |
| H | H | 2-(4,5-dihydro-4 methyl)oxazolyl | 4,843,087 |
| 3 methyl | H | 2-oxazolyl | 4,843,087 |
| 3 bromo | H | 2-oxazolyl | 4,843,087 |
| 3,5 dimethyl | | 3-methyl-5-isoxazolyl | 4,843,087 |
| 2,6 dimethyl | | 3-methyl-5-isoxazolyl | 4,843,087 |
| H | H | 5-methyl-3-isoxazolyl | 4,942,241 |
| H | H | 4-hydroxy phenyl | (Aldrich) |
| H | H | phenyl | (Aldrich) |
| H | H | 5-ethyl-thiazol-2-yl | 5,100,893 |
| H | H | 4,5-dimethyl-thiazol-2-yl | 5,100,893 |
| H | H | 2-ethyl-thiazol-4-yl | 5,100,893 |
| H | H | 5-ethyl-1,3,4-thiadiazol-2-yl | 5,100,893 |
| H | 3-Cl | 3-ethyl-1,2,4-oxadiazol-5-yl | 5,100,893 |
| H | H | 3-cyclopropyl-1,2,4-oxadiazol-5-yl | 5,100,893 |
| H | H | 3-tbutyl-1,2,4-oxadiazolyl | 5,100,893 |
| H | H | 5-ethyl-1,3,4-oxadiazol-2-yl | 5,100,893 |
| H | H | 3-cyclopropyl,2,4-oxadiazol-5-yl | 5,100,893 |
| H | H | 3-ethyl-1,3,4-thiadiazol-5-yl | 5,100,893 |
| H | H | 3-(2hydroxy)propyl-1,2,4-oxadiazol-5-yl | 5,100,893 |
| H | H | 4-ethyl-3-thiazol-2-yl | 5,100,893 |
| H | H | 5-ethyl-3-thiazol-2-yl | 5,100,893 |
| 3-chloro | H | 3-ethyl-1,2,4-oxadiazol-5-yl | 5,100,893 |
| H | H | 4,5-dimethyl-3-thiazol-2-yl | 5,100,893 |
| 2-methoxy | H | 4,5dihydro oxazol-2-yl | 4,843,087 |
| 3-methoxy | H | 4,5dihydro oxazol-2-yl | 4,843,087 |
| 3-chloro | H | 4,5dihydro oxazol-2-yl | 4,843,087 |
| 3-hydroxy | H | 4,5dihydro oxazol-2-yl | 4,843,087 |
| 3,5 di-t-butyl | | 4,5dihydro oxazol-2-yl | 4,843,087 |
| 3-difluoromethyl | H | 4,5dihydro oxazol-2-yl | 4,843,087 |
| 3-hydroxymethyl | H | 4,5dihydro oxazol-2-yl | 4,843,087 |
| 3-carboxy | H | 4,5dihydro oxazol-2-yl | 4,843,087 |
| 2-methyl | 3-hydroxy | 4,5dihydro oxazol-2-yl | 4,843,087 |
| 2,6 dichloro | | 4,5dihydro oxazol-2-yl | 4,843,087 |
| 3,5 difloro | | 4,5dihydro oxazol-2-yl | 4,843,087 |
| 3-chloro | 5-ethynyl | 4,5dihydro oxazol-2-yl | 4,843,087 |

EXAMPLE 20

D. It is contemplated that any known hydroxy (Q) compound can be used to prepare the corresponding triflate which can then be reacted with the compound of example 11B under the conditions of example 11C to form compounds of formula I; examples of such compounds include:

4-hydroxy pyrimidine;

2-hydroxy pyrimidine;

4,6-pyrimidine diol;

2,4-pyrimidine dione (uracil);

2-hydroxy pyridine;

3-hydroxy pyridine;

4-hydroxy pyridine;

2-hydroxy-5-pyridine carboxylic acid;

3-hydroxy-2-pyridine carboxylic acid;

2,4-dihydroxy pyridine;

3-hydroxy pyrazine;

2-hydroxy pyrazine;

2-hydroxy-5-methyl pyrazine;

4-hydroxy-5-methyl pyrimidine;

2-hydroxy-4-methylpyrimidine;

2-hydroxy-4-chloro pyridine;

3-hydroxy-4-methyl pyridine;

3-hydroxy-2-methyl pyrimidine;

5-hydroxypyrimidine;

6-hydroxy pyrimidine;

2-hydroxy pyrazine;

3-hydroxy pyrazine;

2-hydroxy-5-methyl pyrazine;

2-hydroxy-6-methyl pyrazine;

3-hydroxy-6-methyl pyrazine;

3-hydroxy-5-methyl pyrazine;

3-hydroxy-5-methoxy pyrazine;

2-hydroxy-6-methoxy pyrazine;

5-(2-hydroxy pyrazine)carboxylic acid;

2-amino-4-hydroxy pyrimidine (which can be oxidized to 2-nitro-4-hydroxy pyrimidine)

(This list is not exhaustive, but exemplary in nature. Thus nothing in this list is intended to limit the claims thereto.)

BIOLOGICAL PROPERTIES

Biological evaluation of representative compounds of formula I has shown that they possess antipicornaviral activity. They are useful in inhibiting picornavirus replication in vitro and are primarily active against picornaviruses, including enteroviruses, echovirus and coxsackie virus, especially rhinoviruses. The in vitro testing of the representative compounds of the invention against picornaviruses showed that picornaviral replication was inhibited at minimum inhibitory concentrations (MIC) ranging from to micrograms per milliliter (µg/ml).

The MIC values were determined by an automated tissue culture infectious dose 50% (TCID-50) assay. HeLa cells in monoloyers in 96-well cluster plates were infected with a dilution of picornavirus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from picornavirus-induced CPE relative to an untreated picornavirus control.

In the above test procedures, representative compounds of formula I were tested against some the serotypes from either a panel of fifteen human rhinopicornavirus (HRV) serotypes, (noted in the table as panel T) namely, HRV-2, -14, -1A, -1B, -6, -21, -22, -15, -25, -30, -50, -67, -89, -86 and -41 or against some of the serotypes from a panel of 10 human rhinopicornavirus serotypes namely HRV-3, -4, -5, -9, -16, -18, -38, -66, -75 and -67, (noted in the table as panel B) and the MIC value, expressed in micrograms per milliliter (mg/ml), for each rhinopicornavirus serotype was determined for each picornavirus, example 1e is given as an example of the data. Then $MIC_{50}$ and $MIC_{80}$ values, which are the minimum concentrations of the compound required to inhibit 50% and 80%, respectively, of the tested serotypes were determined. The compounds tested were found to exhibit antipicornaviral activity against one or more of these serotypes.

The following Table gives the test results for representative compounds of the invention. The panel of picornaviruses used in the test appears before the the $MIC_{80}$ and $MIC_{50}$ figure and the number of serotypes which the compound is tested against (N) is indicated after the $MIC_{80}$ and $MIC_{50}$ figure.

TABLE

| Ex | Panel | $Mic_{50}$ | $Mic_{80}$ | N |
|---|---|---|---|---|
| 1e | B | 0.149 | 0.663 | 10 |
| 2e | T | 0.185 | 2.84 | 13 |
| 3e | T | 0.0905 | 0.167 | 14 |
| 3f | B | 0.87 | — | 9 |
| 3g | B | 0.41 | 0.61 | 10 |
| 5d | B | 0.082 | 0.627 | 10 |
| 7d | B | 0.1615 | 0.793 | 10 |
| 8d | B | 0.0475 | — | 8 |
| 9d | T | — | 0.283 | 15 |
| 10c | T | 0.48 | 2.293 | 15 |
| 11d | B | 0.082 | 0.627 | 10 |
| 13a | T | 0.064 | 0.618 | 15 |
| 13b | T | 0.073 | 0.122 | 15 |
| 13c | T | 0.036 | 0.353 | 15 |
| 13d | T | 0.161 | 0.29 | 15 |
| 13e | T | 0.043 | 0.133 | 14 |
| 13f | B | 0.0895 | 0.36 | 10 |
| 13g | B | 0.0475 | — | 8 |
| 13h | B | 0.0335 | 0.112 | 10 |
| 13i | T | 0.493 | — | 13 |
| 13j | T | 0.139 | 0.313 | 15 |
| 13k | B | 2.0 | 2.41 | 10 |
| 13l | B | 0.0855 | 0.48 | 10 |
| 13m | B | 0.15 | 0.185 | 9 |
| 14a | T | 0.384 | 0.621 | 9 |
| 14b | B | 0.076 | .4 | 7 |
| 14c | B | 0.12 | 0.076 | 7 |
| 14e | T | 0.02 | 0.18 | 15 |
| 14f | T | 0.281 | 0.957 | 15 |
| 14g | B | 0.136 | .15 | 7 |
| 14h | T | 0.035 | 0.22 | 15 |
| 14i | T | 0.076 | 0.512 | 12 |
| 14j | T | 0.1145 | 0.346 | 12 |
| 14k | B | 0.18 | 0.71 | 7 |
| 15a | T | 0.224 | 3.173 | 15 |
| 15b | T | 0.291 | 1.335 | 11 |
| 15c | T | 0.395 | — | 11 |
| 15d | B | 0.089 | 0.208 | 5 |
| 15e | B | 0.166 | 0.869 | 5 |
| 15f | T | 0.229 | 1.084 | 13 |
| 16b | B | 1.9 | 1.9 | 10 |
| 16d | B | 1.0 | 4.3 | 10 |
| 17e | T | 0.224 | 3.173 | 11 |
| 17g | T | 0.2835 | 0.704 | 14 |

— = insufficient data or inactive

FORMULATIONS OF THE INVENTION

The compounds of formula I can be formulated into compositions, including sustained release compositions together with one or more non-toxic physiologically acceptable carriers, adjuvants or vehicles which are collectively referred to herein as carriers, in any conventional form, using conventional formulation techniques for preparing compositions for treatment of infection or for propylactic use, using formulations well known to the skilled pharmaceutical chemist, for parenteral injection or oral or nasal administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as an aerosal, for example as a nasal or a buccal spray.

Compositions suitable for parenteral injection can comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, polyalkylene glycols and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monostearate and gelatin.

Solid dosage forms for oral administration include capsules, tablets, pills, powders, lozenges and granules which may be dissolved slowly in the mouth, in order to bathe the mouth and associated passages with a solution of the active ingredient. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets and pills, the dosage forms can also comprise buffering agents.

Certain solid dosage forms can be delivered through the inhaling of a powder manually or through a device such as a SPIN-HALER used to deliver disodium cromoglycate (INTAL). When using the latter device, the powder can be encapsulated. When employing a liquid composition, the drug can be delivered through a nebulizer, an aerosol vehicle, or through any device which can divide the composition into discrete portions, for example, a medicine dropper or an atomizer.

Solid compositions of a similar type may also be formulated for use in soft and hard gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They can contain opacifying agents, and can also be of such composition that they release the active compound or compounds in a certain part of the intestinal tract in a delayed manner.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. Also solid formulations can be prepared as a base for liquid formulations. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring and perfuming agents.

Suspensions, in addition to the active compounds, can contain suspending agents, as for example, ethoxylated isostearyl alcohols, polyoxyethylene sorbitol, polyethyleneglycols of varying molecular weights and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures bun liquid at body temperature and, therefore, melt in the rectum or vaginal cavity and release the active component.

Compositions for administration as aerosols are prepared by dissolving a compound of Formula I in water or a suitable solvent, for example an alcohol ether, or other inert solvent, and mixing with a volatile propellant and placing in a pressurized container having a metering valve to release the material in useful droplet size.

The liquefied propellant employed typically one which has a boiling point below ambient temperature at atmospheric pressure. For use in compositions intended to produce aerosols for medicinal use, the liquefied propellant should be non-toxic. Among the suitable liquefied propellants which can be employed are the lower alkanes containing up to five carbon atoms, such as butane and pentane, or a alkyl chloride, such as methyl, ethyl, or propyl chlorides. Further suitable liquefied propellants are the fluorinated and fluorochlorinated alkanes such as are sold under the trademarks "Freon" and "Genetron". Mixtures of the above mentioned propellants can suitably be employed.

Preferred liquefied propellants are chlorine free propellants, for example 134a (tetrafluoroethane) and 227c (heptafluoropropane) which can be used as described above. Typically, one uses a cosolvent, such as an ether, alcohol or glycol in such aerosol formulations.

The specifications for unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are capsules adapted for ingestion or, aerosols with metered discharges, segregated multiples of any of the foregoing, and other forms as herein described.

Compounds of the invention are useful for the prophylaxis and treatment of infections of suspected picornaviral etiologies such as aseptic meningitis, upper respiratory tract infection, enterovirus infections, coxsackievirus, enteroviruses and the like. An effective but non-toxic quantity of the compound is employed in treatment. The dosage of the compound used in treatment depends on the route of administration, e.g., intra nasal, intra bronchial, and the potency of the particular compound.

Dosage forms for topical administration include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated.

It will be appreciated that the starting point for dosage determination, both for prophylaxis and treatment of picornaviral infection, is based on a plasma level of the compound at roughly the minimum inhibitory concentration levels determined for a compound in the laboratory. For example a MIC of 1 µg/mL would give a desired starting plasma level of 0.1 mg/dl and a dose for the average 70 Kg mammal of roughly 5 mg. It is specifically contemplated that dosage range may be from 0.01–1000 mg.

Actual dosage levels of the active ingredient in the compositions can be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors and is readily determined by those skilled in the art.

The formulation of a pharmaceutical dosage form, including determination of the appropriate ingredients to employ in formulation and determination of appropriate levels of active ingredient to use, so as to achieve the optimum bioavailability and longest blood plasma halflife and the like, is well within the purview of the skilled artisan, who normally considers in vivo dose-response relationships when developing a pharmaceutical composition for therapeutic use.

Moreover, it will be appreciated that the appropriate dosage to achieve optimum results of therapy is a matter well within the purview of the skilled artisan who normally considers the dose-response relationship when developing a regimen for therapeutic use. For example the skilled artisan may consider in vitro minimum inhibitory concentrations as a guide to effective plasma levels of the drug. However, this and other methods are all well within the scope of practice of the skilled artisan when developing a pharmaceutical.

It will be understood that the specific dose level for any particular patient will depend upon a variety of factors including the body weight, general health, sex, diet, time and route of administration, rates of absorption and excretion, combination with other drugs and the severity of the disease being treated and is readily determined by the skilled clinician.

When administered prior to infection, that is, prophylactically, it is preferred that the administration be within about 0 to 48 hours prior to infection of the host animal with the pathogenic picornavirus. When administered therapeutically to inhibit an infection it is preferred that the administration be within about a day or two after infection with the pathogenic virus.

The dosage unit administered will be dependent upon the picornavirus for which treatment or prophylaxis is desired, the type of animal involved, its age, health, weight, extent of infection, kind of concurrent treatment, if any, frequency of treatment and the nature of the effect desired.

The compound of the invention also finds utility in preventing the spread of picornaviral infection. The compounds can be used in aerosol sprays applied to contaminated surfaces, to disposable products, such as tissues and the like used by an infected person. In addition the compounds can be used to impregnate household products such as tissues, other paper products, disposable swabs, and the like to prevent the spread of infection by inactivating the picornavirus.

Because compounds of the invention are able to suppress the growth of picornaviruses when added to a medium in which the picornavirus is growing, it is specifically contemplated that compounds of the invention can be used in disinfecting solutions, for example in aqueous solution with a surfactant, to decontaminate surfaces on which polio, Coxsackie, rhinovirus and/or other picornaviruses are present, such surfaces including, but not limited to, hospital glassware, hospital working surfaces, restuarant tables, food service working surfaces, bathroom sinks and anywhere else that it is expected that picornaviruses may be harbored.

Hand contact of nasal mucus may be the most important mode of rhinovirus transmission. Sterilization of the hands of people coming into contact with persons infected with rhinovirus prevents further spread of the disease. It is contemplated that a compound of the invention incorporated into a hand washing or hand care procedure or product, inhibits production of rhinovirus and decreases the likelihood of the transmission of the disease.

We claim:

1. A compound of formula:

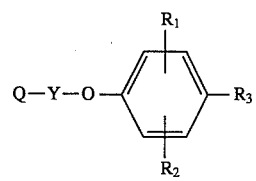

Formula I wherein

Q is chosen from the group consisting of pyridyl, pyrazyl, pyrimidyl, quinolyl, indolyl and 7-azaindolyl or any of these substituted with one or two substituents chosen from alkyl, alkoxy, hydroxy, halo, cyano, nitro, hydroxyalkyl, alkoxyalkyl, alkanoyl, fluoroalkyl or the N-oxide of any of these;

Y is an alkylene bridge of 3–9 carbon atoms;

$R_1$ and $R_2$ are each independently chosen from hydrogen, halo, alkyl, alkenyl, amino, alkylthio, hydroxy, hydroxyalkyl, alkoxyalkyl, alkylthioalkyl, alkylsulfinylalkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkoxycarbonyl, alkyltetrazolyl or substituted or unsubstituted heterocyclyl chosen from benzoxazolyl oxazolyl oxadiazolyl isoxazolyl, wherein the substitution is with alkyl, alkoxyalkyl, cycloalkyl, halo alkyl, hydroxyalkyl, alkoxy, hydroxy, furyl, thienyl or fluoroalkyl; or a pharmaceutically acceptable acid addition salt thereof.

2. A compound according to claim 1 wherein Y is a linear hydrocarbon chain of 3 to five carbons.

3. A compound according to claim 2 wherein $R_3$ is substituted oxadiazolyl or tetrazolyl.

4. A compound according to claim 3 wherein $R_3$ is chosen from the group consisting of 5-trifluoromethyl-1,2,4-oxadiazolyl, 5-fluoromethyl-1,2,4-oxadiazolyl, 5-difluoromethyl-1,2,4-oxadiazolyl and 5-methyl-2H-tetrazolyl.

5. A compound according to claim 4 wherein Q is unsubstituted or singly substituted or the N-oxide thereof.

6. A compound according to claim 5 wherein $R_1$ and $R_2$ represent 3,5-dimethyl and Y is 1,3-propylene.

7. A compound according to claim 6 wherein Q is 2-pyridyl or 3-pyridyl singly substituted with fluoro, methyl or trifluoromethyl.

8. A pharmaceutical composition containing as an active ingredient an antipicornavirally effective amount of a compound according to claim 1.

9. A pharmaceutical composition containing as an active ingredient an antipicornavirally effective amount of a compound according to claim 3.

10. A pharmaceutical composition containing as an active ingredient an antipicornavirally effective amount of a compound according to claim 5.

11. A pharmaceutical composition containing as an active ingredient an antipicornavirally effective amount of a compound according to claim 7.

12. A method of preventing or treating picornaviral infection in a mammalian host comprising administering an antipicornavirally effective amount of a compound according to claim 1.

13. A method of preventing or treating picornaviral infection in a mammalian host comprising administering an antipicornavirally effective amount of a compound according to claim 3.

14. A method of preventing or treating picornaviral infection in a mammalian host comprising administering an antipicornavirally effective amount of a compound according to claim 5.

15. A method of preventing or treating picornaviral infection in a mammalian host comprising administering an antipicornavirally effective amount of a compound according to claim 7.

16. A method of combating picornaviruses comprising contacting the locus of said viruses with an antipicornavirally effective amount of a compound according to claim 1.

17. A method of combating picornaviruses comprising contacting the locus of said viruses with an antipicornavirally effective amount of a compound according to claim 3.

18. A method of combating picornaviruses comprising contacting the locus of said viruses with an antipicornavirally effective amount of a compound according to claim 5.

19. A method of combating picornaviruses comprising contacting the locus of said viruses with an antipicornavirally effective amount of a compound according to claim 7.

* * * * *